US008986951B2

(12) United States Patent
Hohlbaum et al.

(10) Patent No.: US 8,986,951 B2
(45) Date of Patent: Mar. 24, 2015

(54) TEAR LIPOCALIN IN MUTEINS BINDING IL-4 R ALPHA

(75) Inventors: Andreas Hohlbaum, Paunzhausen (DE); Alexandra Baehre, Farum (DK); Gabriele Matschiner, Munich (DE); Stefan Trentmann, Allershausen (DE); Klaus Kirchfeld, Petershausen (DE); Hans-Juergen Christian, Moosburg (DE)

(73) Assignee: Pieris AG, Freising-Weihenstephan (DE)

( * ) Notice: Subject to any disclaimer, the term of this patent is extended or adjusted under 35 U.S.C. 154(b) by 0 days.

(21) Appl. No.: 13/702,792

(22) PCT Filed: Jun. 8, 2011

(86) PCT No.: PCT/EP2011/059420
§ 371 (c)(1),
(2), (4) Date: Dec. 7, 2012

(87) PCT Pub. No.: WO2011/154420
PCT Pub. Date: Dec. 15, 2011

(65) Prior Publication Data
US 2013/0085113 A1  Apr. 4, 2013

Related U.S. Application Data

(60) Provisional application No. 61/352,461, filed on Jun. 8, 2010.

(51) Int. Cl.
| | |
|---|---|
| *C12P 21/06* | (2006.01) |
| *C07K 14/435* | (2006.01) |
| *C07K 14/47* | (2006.01) |
| *C12N 9/16* | (2006.01) |
| *A61K 38/17* | (2006.01) |
| *C12N 15/09* | (2006.01) |
| *C12P 21/02* | (2006.01) |

(52) U.S. Cl.
CPC ............. *C07K 14/435* (2013.01); *C07K 14/47* (2013.01); *C12N 9/16* (2013.01)
USPC ...... 435/69.1; 435/320.1; 435/325; 514/21.2; 530/350; 536/23.5

(58) Field of Classification Search
None
See application file for complete search history.

(56) References Cited

U.S. PATENT DOCUMENTS

| | | | |
|---|---|---|---|
| 5,728,553 A | 3/1998 | Goodey et al. | |
| 6,177,074 B1 | 1/2001 | Glue et al. | |
| 6,403,564 B1 | 6/2002 | Ganguly et al. | |
| 2003/0069395 A1 | 4/2003 | Sato et al. | |

FOREIGN PATENT DOCUMENTS

| | | |
|---|---|---|
| EP | 0 330 451 A2 | 8/1989 |
| EP | 0 361 991 A2 | 4/1990 |
| WO | WO 99/16873 A1 | 4/1999 |
| WO | WO 99/64016 A1 | 12/1999 |
| WO | WO 00/75308 A1 | 12/2000 |
| WO | WO 03/029462 A1 | 4/2003 |
| WO | WO 03/029463 A2 | 4/2003 |
| WO | WO 03/029471 A1 | 4/2003 |
| WO | WO 2005/019254 A1 | 3/2005 |
| WO | WO 2005/019255 A1 | 3/2005 |
| WO | WO 2005/019256 A2 | 3/2005 |
| WO | WO 2006/056464 A2 | 6/2006 |
| WO | WO 2007/038619 A2 | 4/2007 |
| WO | WO 2008/015239 A2 | 2/2008 |

OTHER PUBLICATIONS

Wells, Biochemistry, 1990, vol. 29, pp. 8509-8517.*
Bork, Genome Research , 2000, vol. 10, pp. 398-400.*
Skolnick et al., Trends in Biotech, 2000, vol. 18(1):34-39.*
Doerks et al., Trends in Genetics, 1998, vol. 14, pp. 248-250.*
Tokuriki and Tawflik, Current Opinion in Structural Biology 2009, 19: 596-604.*
Altschul et al., "Gapped BLAST and PSI-BLAST: a new generation of protein database search programs," Nucl. Acids Res., 1997, 25(17):3389-3402.
Altschul et al., "Basic Local Alignment Search Tool," J. Mol. Biol., 1990, 215:403-410.
Altuvia et al,. "Ranking Potential Binding Peptides to MCH Molecules by a Computational Threading Approach. " J. Mol. Biol., 1995, 249:244-250.
Amstutz et al., "In vitro display technologies: novel developments and applications," Curr. Opin. Biotechnol., 2001, 12:400-405.
Bittker et al., "Nucleic acid evolution and minimization by nonhomologous random recombination," Nat. Biotechnol., Oct. 2002, 20:1024-1029.
Breustedt et al., "The 1.8-Å Crystal Structure of Human Tear Lipocalin Reveals an Extended Branched Cavity with Capacity for Multiple Ligands," J. Biol. Chem., Jan. 7, 2005, 280(1):484-493.
Broders et al., "Hyperphage. Improving antibody presentation in phage display," Methods Mol. Biol., 2003, 205:295-302.
Bruckdorfer et al., "From Production of Peptides in Milligram Amounts for Research to Multi-Tons Quantities for Drugs of the Future," Curr. Pharm. Biotechnol., 2004, 5:29-43.

(Continued)

*Primary Examiner* — Bridget E Bunner
*Assistant Examiner* — Fozia Hamud
(74) *Attorney, Agent, or Firm* — Foley & Lardner LLP

(57) ABSTRACT

The present invention relates to novel muteins derived from human tear lipocalin, which bind to IL 4 receptor alpha. The sequences of the muteins comprise particular combinations of amino acids. In particular a mutated amino acid residue is present at any one or more of the sequence positions 27, 28, 30, 31, 33, 53, 57, 61, 64, 66, 80, 83, 104-106 and 108 of the linear polypeptide sequence of the mature human tear lipocalin. A mutated amino acid residue is also present at any 2 or more of the sequence positions 26, 32, 34, 55, 56, 58 and 63 of the linear polypeptide sequence of the mature human tear lipocalin. The invention also provides a corresponding nucleic acid molecule encoding such a mutein and a method for producing such a mutein and its encoding nucleic acid molecule.

21 Claims, 10 Drawing Sheets

(56) References Cited

OTHER PUBLICATIONS

Dennis et al., "Albumin Binding as a General Strategy for Improving the Pharmacokinetics of Proteins," J. Biol. Chem., Sep. 20, 2002, 277(38):35035-35043.
Dodel et al., "Immunotherapy for Alzheimer's disease," Lancet Neurology, Apr. 2003, 2:215-220.
Flower, Darren R., "The lipocalin protein family: structure and function," Biochem. J., 1996, 318:1-14.
Flower et al., "The lipocalin protein family: structural and sequence overview," Biochimica et Biophysica Acta, 2000, 1482:9-24.
Fuertges et al., :The Clinical Efficacy of Poly(Ethylene Glycol)-Modified Proteins,: J. Control. Release, 1990, 11:139-148.
Gaillard et al., "Targeted delivery across the blood-brain barrier," Expert Opin Drug Deliv., 2005, 2(2):299-309.
Gaillard et al., "Diphtheria toxin receptor-targeted brain drug delivery," International Congress Series., 2005, 1277:185-198.
Garland et al., "Phase I Trial of Intravenous IL-4 Psudomonas Exotoxin Protein (NBI-3001) in Patients with Advanced Solid Tumors That Express the IL-4 Receptor," J. Immunother., Jul./Aug. 2005, 28(4):376-381.
Gasymov et al., "Binding studues of tear lipocalin: the role of the conserved tryptophan in maintaining structure, stability and ligand affinity," Biochimica et Biophysica Acta, 1999, 1433:307-320.
Glasgow et al., "Tear lipocalins bind a broad array of lipid ligands," Current Eye Research, 1995, 14:363-372.
Hackbarth et al., "S-peptide epitope tagging for protein purification, expression monitoring, and localization in mammalian cells," BioTechniques, Nov. 2004, 37:835-839.
Husain et al., "Complete Regression of Established Human Gliobastoma Tumor Xenograft by Interleukin-4 Toxin Therapy," Cancer Research, Aug. 15, 1998, 58:3649-3653.
Husain et al., "Interleukin-4 receptor-directed cytotoxin therapy of AIDS-associated Kaposi's sarcoma tumors in xenograft model," Nature Medicine, Jul. 1999, 5(7):817-822.
Kawakami et al., "Internalization property of interleukin-4 receptor alpha chain increases cytotoxic effect of interleukin-4 receptor-targeted cytotoxin in cancer cells," Clinical Cancer Research, Jan. 1, 2002, 8(1):258-266.
Kawakami et al., "Structure, Function, and Targeting of Interleukin 4 Receptors on Human Head and Neck Cancer Cells," Cancer Research, Jun. 1, 2000, 60:2981-2897.
Kioi et al., "Expression and Targeting of Interleukin-4 Receptor for Primary and Advanced Ovarian Cancer Therapy," Cancer Research, Sep. 15, 2005, 65(18):8388-8396.
Koenig et al., "Use of an albumin-binding domain for the selective immobilization of recombinant capture antibody fragments on ELISA plates," Journal of Immunological Methods, 1998, 218:73-83.
Koller et al., "Epithelial interleukin-4 receotpr expression promots colon tumor growth," Carcinogenesis, Jun. 1, 2010, 31(6):1010-1017.
Lefort et al., "IL-13 and IL-4 share signal transduction elements as well as receptor components in TF-1 cells," FEBS Letters, 1995, 366:122-126.
Lowman, H.B. "Bacteriophage display and discovery of peptides leads for drug development," Annu. Rev. Biophys. Biomol. Struct., 1997, 26:401-424.
Mateo et al., "Removal of Amphipathic Epitopes from Genetically Engineered Antibodies: Production of Modified Immunoglobulins with Reduced Immunogenicity," Hybridoma, 2000, 19(6):463-471.
Meidan et al., "Emerging Technologies in Transdermal Therapeutics," Am. J. Ther., 2004, 11(4):312-316.
Murakami et al., "Random insertion and deletion of arbitrary number of bases for codon-based random mutation of DNAs," Nat. Biotechnol., Jan. 2002, 20:76-81.

Osborn et al., "Pharmacokinetic and Pharmacodynamic Studies of a Human Serum Albumin-Interferon-α Fusion Protein in Cynomolgus Monkeys," J. Pharmacol. Exp. Ther., 2002, 303(2):540-548.
Pervaiz et al., "Homology and structure-function correlations between alpha1-acid glycoprotein and serum retinol-binding protein and its relatives," FASEB J., 1987, 1:209-214.
Pini et al., "Phage Display and Colony Filter Screening for High-Throughput Selection of Antibody Libraries," Comb. Chem. High Throughput Screen., 2002, 5:503-510.
Puri et al., "Preclinical Development of a Recombinant Toxia Containing circularly Permuted Interleukin 4 and Truncated Pseudomonas Exotoxin for Therapy of Malignant Astrocytoma," Cancer Research, Dec. 15, 1996, 56:5631-5637.
Rand et al., "Intratumoral Administration of Recombinant Circularly Permuted Interleuki-4-Pseudomonas Exotoxin in Patients with High-Grade Glioma," Clinical Cancer Research, Jun. 2000, 6:2157-2165.
Redl, Bernhard," Human tear lipocalin," Biochimica et Biophysica Acta, 2000, 1482:241-248.
Redl et al., "cDNA Cloning and Sequencing Reveals Human Tear Prealbumin to Be a Member of the Lipophilic-ligand Carrier Protein Superfamily," J. Biol. Chem., Oct. 5, 1992, 267(28):20282-20287.
Rodi et al., "Phage-display technology—finding a needle in a vast molecular haystack," Curr. Opin. Biotechnol., 1999, 10:87-93.
Schlehuber et al., "A Novel Type of Receptor Protein, Based on the Lipocalin Scaffold, with Specificity for Digoxigenin," J. Mol. Biol., 2000, 297:1105-1120.
Schlehuber et al., "Duocalins, engineered ligand-binding proteins with dual specificity derived from the lipocalin fold," Biol. Chem., Sep. 2001, 382:1335-1342.
Schlehuber et al., "Tuning ligand affinity, specificity, and folding stability of an engineered lipocalin variant—a so-called 'anticalin'—using a molecular random approach," Biophysical Chemistry, 2002, 96:213-228.
Schmidt et al., "Molecular Interaction Between the Strep-tag Affinity Peptide and its Cognate Target, Streptavidin," J. Mol. Biol., 1996, 255:753-766.
Skerra, Arne, "'Anticalins': a new class of engineered ligand-binding proteins with antibody-like properties," J. Biotechnol., 2001, 74:257-275.
Skerra, Arne, "Lipocalins as a scaffold," Biochimica et Biophysica Acta, 2000, 1482:337-350.
Smith et al., "Identification of Common Molecular Subsequences," J. Mol. Biol., 1981, 147:195-197.
Strome et al., "Interleukin 4 Receptor-directed Cytotoxin Therapy for Human Head and Neck Squamous Cell Carcinoma in Animal Models," Clinical Cancer Research, Jan. 2002, 8:281-286.
Vajo et al., "Genetically Engineered Insulin Analogs: Diabetes in the New Millenium," Pharmacol. Rev., 2000, 52(1):1-9.
Venturi et al., "High Level Production of Functional Antibody Fab Fragments in an Oxidizing Bacterial Cytoplasm," J. Mol. Biol., 2002, 315:1-8.
Wang et al., "Expanding the genetic code," Chem. Comm., 2002, 1:1-11.
Wang et al., "Expanding the Genetic Code of Escherichia coli," Science, Apr. 20, 2001, 292:498-500.
Wilson et al., "The use of mRNA display to select high-affinity protein-binding peptides," Proc. Natl. Acad. Sci. USA, Mar. 27, 2001, 98(7):3750-3755.
You et al., "Post-translation modification of proteins in tears," Electrophoresis, 2010, 31:1853-1861.
Zaccolo et al., "An Approach to Random Mutagenesis of DNA Using Mixtures of Triphosphate Derivatives of Nucleoside Analogues," J. Mol. Biol., 1996, 255:589-603.

* cited by examiner

```
MKKTAIAIAV  ALAGFATVAQ  AASDEEIQDV  SGTWYLKAMT  VDSRCPRAYY
SSVTPMTLTT  LEGGNLEAKF  TAQRSGRWQE  YKLVLEKTDE  PGKYTASGGR
HVAYIIRSHV  KDHYIFHSEG  LCPGQPVPGV  WLVGRDPKNN  LEALEDFEKA
AGARGLSTES  ILIPRQSETS  SPGSAWSHPQ  FEK
```

FIG. 1

| SwissProt P31025 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|
| AB4004 | 5 | 6 | 7 | 8 | 9 | 10 | 11 | 12 | 13 | 14 | 15 | 16 | 17 | 18 | 19 |
| wt TLc26 | A | S | D | E | E | I | Q | D | V | S | G | T | W | Y | L |
| M3-B24(PSM) | 5 | 6 | 7 | 8 | 9 | 10 | 11 | 12 | 13 | 14 | 15 | 16 | 17 | 18 | 19 |
| S191.4-B24 | A | S | D | E | E | I | Q | D | V | S | G | T | W | Y | L |
| S351.5-M21 | A | S | D | E | E | I | Q | D | V | S | G | T | W | Y | L |
| S276.2-K04 | A | S | D | E | E | I | Q | D | V | S | G | T | W | Y | L |
| S308.5-K12 | A | S | D | E | E | I | Q | D | V | S | G | T | W | Y | L |
| S308.5-F08 | A | S | D | E | E | I | Q | D | V | S | G | T | W | Y | L |
| S308.5-L4 | A | S | D | E | E | I | Q | D | V | S | G | T | W | Y | L |
| S308.5-L20 | A | S | D | E | E | I | Q | D | V | S | G | T | W | Y | L |
| S308.5-N1 | A | S | D | E | E | I | Q | D | V | S | G | T | W | Y | L |
| S308.3-O10 | A | S | D | E | E | I | Q | D | V | S | G | T | W | Y | L |
| S308.5-N20 | A | S | D | E | E | I | Q | D | V | S | G | T | W | Y | L |

| SwissProt P31025 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|
| AB4004 | 20 | 21 | 22 | 23 | 24 | 25 | 26 | 27 | 28 | 29 | 30 | 31 | 32 | 33 | 34 |
| wt TLc26 | K | A | M | T | V | D | R | E | F | P | E | M | N | L | E |
| M3-B24(PSM) | 20 | 21 | 22 | 23 | 24 | 25 | 26 | 27 | 28 | 29 | 30 | 31 | 32 | 33 | 34 |
| S191.4-B24 | K | A | M | T | V | D | S | R | C | P | R | A | Y | Y | S |
| S351.5-M21 | K | A | M | T | V | D | S | R | C | P | R | A | Y | Y | E |
| S276.2-K04 | K | A | M | T | V | D | P | R | C | P | R | A | Y | Y | S |
| S308.5-K12 | K | A | M | T | V | D | L | R | C | P | R | A | F | Y | W |
| S308.5-F08 | K | A | M | T | V | D | S | R | C | P | R | A | V | Y | N |
| S308.5-L4 | K | A | M | T | V | D | S | R | C | P | R | A | Y | Y | V |
| S308.5-L20 | K | A | M | T | V | D | N | R | C | P | R | A | K | Y | D |
| S308.5-N1 | K | A | M | T | V | D | Y | R | C | P | R | A | Y | Y | H |
| S308.3-O10 | K | A | M | T | V | D | K | R | C | P | R | A | Y | Y | R |
| S308.5-N20 | K | A | M | T | V | D | E | R | C | P | R | A | H | Y | G |

FIG. 2A

| SwissProt P31025 | 53 | 54 | 55 | 56 | 57 | 58 | 59 | 60 | 61 | 62 | 63 | 64 | 65 | 66 | 67 |
|---|---|---|---|---|---|---|---|---|---|---|---|---|---|---|---|
| AB4004 | 35 | 36 | 37 | 38 | 39 | 40 | 41 | 42 | 43 | 44 | 45 | 46 | 47 | 48 | 49 |
| wt TLc26 | S | V | T | P | M | T | L | T | T | L | E | G | G | N | L |
| M3-B24(PSM) | 35 | 36 | 37 | 38 | 39 | 40 | 41 | 42 | 43 | 44 | 45 | 46 | 47 | 48 | 49 |
| S191.4-B24 | S | V | T | P | M | T | L | T | T | L | E | G | G | N | L |
| S351.5-M21 | S | V | T | P | M | T | L | T | T | L | E | G | G | N | L |
| S276.2-K04 | S | V | T | P | M | T | L | T | T | L | E | G | G | N | L |
| S308.5-K12 | S | V | T | P | M | T | L | T | T | L | E | G | G | N | L |
| S308.5-F08 | S | V | T | P | M | T | L | T | T | L | E | G | G | N | L |
| S308.5-L4 | S | V | T | P | M | T | L | T | T | L | E | G | G | N | L |
| S308.5-L20 | S | V | T | P | M | T | L | T | T | L | E | G | G | N | L |
| S308.5-N1 | S | V | T | P | M | T | L | T | T | L | E | G | G | N | L |
| S308.3-O10 | S | V | T | P | M | T | L | T | T | L | E | G | G | N | L |
| S308.5-N20 | S | V | T | P | M | T | L | T | T | L | E | G | G | N | L |

| SwissProt P31025 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|
| AB4004 | 50 | 51 | 52 | 53 | 54 | 55 | 56 | 57 | 58 | 59 | 60 | 61 | 62 | 63 | 64 |
| wt TLc26 | E | A | K | V | T | M | L | I | S | G | R | S | Q | E | V |
| M3-B24(PSM) | 50 | 51 | 52 | 53 | 54 | 55 | 56 | 57 | 58 | 59 | 60 | 61 | 62 | 63 | 64 |
| S191.4-B24 | E | A | K | F | T | A | Q | R | S | G | R | W | Q | E | Y |
| S351.5-M21 | E | A | K | L | T | L | Q | R | K | G | R | W | Q | E | M |
| S276.2-K04 | E | A | K | F | T | A | Q | R | S | G | R | W | Q | K | Y |
| S308.5-K12 | E | A | K | F | T | A | L | R | I | G | R | W | Q | S | Y |
| S308.5-F08 | E | A | K | F | T | A | Q | R | K | G | R | W | Q | K | Y |
| S308.5-L4 | E | A | K | F | T | A | A | R | I | G | R | W | Q | S | Y |
| S308.5-L20 | E | A | K | F | T | A | H | R | R | G | R | W | Q | Q | Y |
| S308.5-N1 | E | A | K | F | T | A | H | R | A | G | R | W | Q | K | Y |
| S308.3-O10 | E | A | K | F | T | A | K | R | N | G | R | W | Q | P | Y |
| S308.5-N20 | E | A | K | F | T | A | M | R | L | G | R | W | Q | K | Y |

FIG. 2B

| SwissProt P31025 | 83 | 84 | 85 | 86 | 87 | 88 | 89 | 90 | 91 | 92 | 93 | 94 | 95 | 96 | 97 |
|---|---|---|---|---|---|---|---|---|---|---|---|---|---|---|---|
| AB4004 | 65 | 66 | 67 | 68 | 69 | 70 | 71 | 72 | 73 | 74 | 75 | 76 | 77 | 78 | 79 |
| wt TLc26 | K | A | V | L | E | K | T | D | E | P | G | K | Y | T | A |
| M3-B24(PSM) | 65 | 66 | 67 | 68 | 69 | 70 | 71 | 72 | 73 | 74 | 75 | 76 | 77 | 78 | 79 |
| S191.4-B24 | K | L | V | L | E | K | T | D | E | P | G | K | Y | T | A |
| S351.5-M21 | K | D | V | L | E | K | T | D | E | P | G | K | Y | T | A |
| S276.2-K04 | K | L | V | L | E | K | T | D | E | P | G | K | Y | T | A |
| S308.5-K12 | K | L | V | L | E | K | T | D | E | P | G | K | Y | T | A |
| S308.5-F08 | K | L | V | L | E | K | T | D | E | P | G | K | Y | T | A |
| S308.5-L4 | K | L | V | L | E | K | T | D | E | P | G | K | Y | T | A |
| S308.5-L20 | K | L | V | L | E | K | T | D | E | P | G | K | Y | T | A |
| S308.5-N1 | K | L | V | L | E | K | T | D | E | P | G | K | Y | T | A |
| S308.3-O10 | K | L | V | L | E | K | T | D | E | P | G | K | Y | T | A |
| S308.5-N20 | K | L | V | L | E | K | T | D | E | P | G | K | Y | T | A |

| SwissProt P31025 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|
| AB4004 | 80 | 81 | 82 | 83 | 84 | 85 | 86 | 87 | 88 | 89 | 90 | 91 | 92 | 93 | 94 |
| wt TLc26 | D | G | G | K | H | V | A | Y | I | I | R | S | H | V | K |
| M3-B24(PSM) | 80 | 81 | 82 | 83 | 84 | 85 | 86 | 87 | 88 | 89 | 90 | 91 | 92 | 93 | 94 |
| S191.4-B24 | S | G | G | R | H | V | A | Y | I | I | R | S | H | V | K |
| S351.5-M21 | S | G | G | R | H | V | A | Y | I | I | R | S | H | V | K |
| S276.2-K04 | S | G | G | R | H | V | A | Y | I | I | R | S | H | V | K |
| S308.5-K12 | S | G | G | R | H | V | A | Y | I | I | R | S | H | V | K |
| S308.5-F08 | S | G | G | R | H | V | A | Y | I | I | R | S | H | V | K |
| S308.5-L4 | S | G | G | R | H | V | A | Y | I | I | R | S | H | V | K |
| S308.5-L20 | S | G | G | R | H | V | A | Y | I | I | R | S | H | V | K |
| S308.5-N1 | S | G | G | R | H | V | A | Y | I | I | R | S | H | V | K |
| S308.3-O10 | S | G | G | R | H | V | A | Y | I | I | R | S | H | V | K |
| S308.5-N20 | S | G | G | R | H | V | A | Y | I | I | R | S | H | V | K |

FIG. 2C

| SwissProt P31025 | 113 | 114 | 115 | 116 | 117 | 118 | 119 | 120 | 121 | 122 | 123 | 124 | 125 | 126 | 127 |
|---|---|---|---|---|---|---|---|---|---|---|---|---|---|---|---|
| AB4004 | 95 | 96 | 97 | 98 | 99 | 100 | 101 | 102 | 103 | 104 | 105 | 106 | 107 | 108 | 109 |
| wt TLc26 | D | H | Y | I | F | Y | S | E | G | E | L | H | G | K | P |
| M3-B24(PSM) | 95 | 96 | 97 | 98 | 99 | 100 | 101 | 102 | 103 | 104 | 105 | 106 | 107 | 108 | 109 |
| S191.4-B24 | D | H | Y | I | F | H | S | E | G | L | C | P | G | Q | P |
| S351.5-M21 | D | H | Y | I | F | Y | S | E | G | L | C | P | G | Q | P |
| S276.2-K04 | D | H | Y | I | F | H | S | E | G | L | C | P | G | Q | P |
| S308.5-K12 | D | H | Y | I | F | H | S | E | G | L | C | P | G | Q | P |
| S308.5-F08 | D | H | Y | I | F | H | S | E | G | L | C | P | G | Q | P |
| S308.5-L4 | D | H | Y | I | F | H | S | E | G | L | C | P | G | Q | P |
| S308.5-L20 | D | H | Y | I | F | H | S | E | G | L | C | P | G | Q | P |
| S308.5-N1 | D | H | Y | I | F | H | S | E | G | L | C | P | G | Q | P |
| S308.3-O10 | D | H | Y | I | F | H | S | E | G | L | C | P | G | Q | P |
| S308.5-N20 | D | H | Y | I | F | H | S | E | G | L | C | P | G | Q | P |

| SwissProt P31025 | 128 | 129 | 130 | 131 | 132 | 133 | 134 | 135 | 136 | 137 | 138 | 139 | 140 | 141 | 142 |
|---|---|---|---|---|---|---|---|---|---|---|---|---|---|---|---|
| AB4004 | 110 | 111 | 112 | 113 | 114 | 115 | 116 | 117 | 118 | 119 | 120 | 121 | 122 | 123 | 124 |
| wt TLc26 | V | P | G | V | W | L | V | G | R | D | P | K | N | N | L |
| M3-B24(PSM) | 110 | 111 | 112 | 113 | 114 | 115 | 116 | 117 | 118 | 119 | 120 | 121 | 122 | 123 | 124 |
| S191.4-B24 | V | P | G | V | W | L | V | G | R | D | P | K | N | N | L |
| S351.5-M21 | V | P | G | V | W | L | V | G | R | D | P | K | N | N | L |
| S276.2-K04 | V | P | G | V | W | L | V | G | R | D | P | K | N | N | L |
| S308.5-K12 | V | P | G | V | W | L | V | G | R | D | P | K | N | N | L |
| S308.5-F08 | V | P | G | V | W | L | V | G | R | D | P | K | N | N | L |
| S308.5-L4 | V | P | G | V | W | L | V | G | R | D | P | K | N | N | L |
| S308.5-L20 | V | P | G | V | W | L | V | G | R | D | P | K | N | N | L |
| S308.5-N1 | V | P | G | V | W | L | V | G | R | D | P | K | N | N | L |
| S308.3-O10 | V | P | G | V | W | L | V | G | R | D | P | K | N | N | L |
| S308.5-N20 | V | P | G | V | W | L | V | G | R | D | P | K | N | N | L |

FIG. 2D

| SwissProt P31025 | 143 | 144 | 145 | 146 | 147 | 148 | 149 | 150 | 151 | 152 | 153 | 154 | 155 | 156 | 157 |
|---|---|---|---|---|---|---|---|---|---|---|---|---|---|---|---|
| AB4004 | 125 | 126 | 127 | 128 | 129 | 130 | 131 | 132 | 133 | 134 | 135 | 136 | 137 | 138 | 139 |
| wt TLc26 | E | A | L | E | D | F | E | K | A | A | G | A | R | G | L |
| M3-B24(PSM) | 125 | 126 | 127 | 128 | 129 | 130 | 131 | 132 | 133 | 134 | 135 | 136 | 137 | 138 | 139 |
| S191.4-B24 | E | A | L | E | D | F | E | K | A | A | G | A | R | G | L |
| S351.5-M21 | E | A | L | E | D | F | E | K | A | A | G | A | R | G | L |
| S276.2-K04 | E | A | L | E | D | F | E | K | A | A | G | A | R | G | L |
| S308.5-K12 | E | A | L | E | D | F | E | K | A | A | G | A | R | G | L |
| S308.5-F08 | E | A | L | E | D | F | E | K | A | A | G | A | R | G | L |
| S308.5-L4 | E | A | L | E | D | F | E | K | A | A | G | A | R | G | L |
| S308.5-L20 | E | A | L | E | D | F | E | K | A | A | G | A | R | G | L |
| S308.5-N1 | E | A | L | E | D | F | E | K | A | A | G | A | R | G | L |
| S308.3-O10 | E | A | L | E | D | F | E | K | A | A | G | A | R | G | L |
| S308.5-N20 | E | A | L | E | D | F | E | K | A | A | G | A | R | G | L |

| SwissProt P31025 | 158 | 159 | 160 | 161 | 162 | 163 | 164 | 165 | 166 | 167 | 168 | 169 | 170 | 171 | 172 |
|---|---|---|---|---|---|---|---|---|---|---|---|---|---|---|---|
| AB4004 | 140 | 141 | 142 | 143 | 144 | 145 | 146 | 147 | 148 | 149 | 150 | 151 | 152 | 153 | 154 |
| wt TLc26 | S | T | E | S | I | L | I | P | R | Q | S | E | T | S | S |
| M3-B24(PSM) | 140 | 141 | 142 | 143 | 144 | 145 | 146 | 147 | 148 | 149 | 150 | 151 | 152 | 153 | 154 |
| S191.4-B24 | S | T | E | S | I | L | I | P | R | Q | S | E | T | S | S |
| S351.5-M21 | S | T | E | S | I | L | I | P | R | Q | S | E | T | S | S |
| S276.2-K04 | S | T | E | S | I | L | I | P | R | Q | S | E | T | S | S |
| S308.5-K12 | S | T | E | S | I | L | I | P | R | Q | S | E | T | S | S |
| S308.5-F08 | S | T | E | S | I | L | I | P | R | Q | S | E | T | S | S |
| S308.5-L4 | S | T | E | S | I | L | I | P | R | Q | S | E | T | S | S |
| S308.5-L20 | S | T | E | S | I | L | I | P | R | Q | S | E | T | S | S |
| S308.5-N1 | S | T | E | S | I | L | I | P | R | Q | S | E | T | S | S |
| S308.3-O10 | S | T | E | S | I | L | I | P | R | Q | S | E | T | S | S |
| S308.5-N20 | S | T | E | S | I | L | I | P | R | Q | S | E | T | S | S |

FIG. 2E

| | | |
|---|---|---|
| SwissProt P31025 | 173 | 174 |
| AB4004 | 155 | 156 |
| wt TLc26 | P | G |
| M3-B24(PSM) | 155 | 156 |
| S191.4-B24 | P | G |
| S351.5-M21 | P | G |
| S276.2-K04 | P | G |
| S308.5-K12 | P | G |
| S308.5-F08 | P | G |
| S308.5-L4 | P | G |
| S308.5-L20 | P | G |
| S308.5-N1 | P | G |
| S308.3-O10 | P | G |
| S308.5-N20 | P | G |

FIG. 2F

|  | IC50 TF1-Proliferation assay IL-13 (nM) | IC50 TF1-Proliferation assay IL-4 (nM) | Biacore affinity KD (M) |
|---|---|---|---|
| S276.2 K04 | 14.8 | 3.6 | 2.30E-11 |
| S308.5 F08 | 7.4 | 3.8 | 2.01E-11 |
| S308.5 N01 | 17.7 | 4.4 | 2.41E-11 |
| S308.5 L20 | 14.4 | 5.3 | 2.49E-11 |
| S308.5 L04 | 22.9 | 5.7 | 7.24E-11 |
| S308.5 N20 | 27.6 | 5.9 | 3.48E-11 |
| S308.3 O10 | 15.1 | 7.5 | 1.32E-12 |
| S191.4 B24 | 35.9 | 9.1 | 1.10E-10 |

FIG. 4

SEQUENCE LISTING

<160> NUMBER OF SEQ ID NOS: 20

<210> SEQ ID NO 1
<211> LENGTH: 3700
<212> TYPE: DNA
<213> ORGANISM: Artificial
<220> FEATURE:
<223> OTHER INFORMATION: Expression vector pTLPC10

<400> SEQUENCE: 1

```
ccatcgaatg gccagatgat taattcctaa ttttttgttga cactctatca ttgatagagt      60
tattttacca ctccctatca gtgatagaga aaagtgaaat gaatagttcg acaaaaatct     120
agataacgag ggcaaaaaat gaaaaagaca gctatcgcga ttgcagtggc actggctggt     180
ttcgctaccg tagcgcaggc cgacgcatcg atgaccggtg gtcagcagat gggtgcctca     240
gacgaggaga ttcaggatgt gtcagggacg tggtatctga aggccatgac ggtggacagg     300
gagttccctg agatgaatct ggaatcggtg acacccatga ccctcacgac cctggaaggg     360
ggcaacctgg aagccaaggt caccatgctg ataagtggcc ggagccagga ggtgaaggcc     420
gtcctggaga aaactgacga gccgggaaaa tacacggccg acggggggcaa gcacgtggca     480 tacatcatca ggtcgcacgt gaaggaccac tacatctttt actctgaggg cgagctccac     540
gggaagccgg tcccaggggt gtggctcgtg ggcagagacc caagaacaa cctggaagcc     600 ttggaggact ttgagaaagc cgcaggagcc cgcggactca gcacggagag catcctcatc     660
cccaggcaga gcgaaaccag ctctccaggg agcgcttggt ctcacccgca gttcgaaaaa     720
taataagctt gacctgtgaa gtgaaaaatg gcgcacattg tgcgacattt tttttgtctg     780
ccgtttaccg ctactgcgtc acggatctcc acgcgccctg tagcggcgca ttaagcgcgg     840
cgggtgtggt ggttacgcgc agcgtgaccg ctacacttgc cagcgcccta gcgcccgctc     900
ctttcgcttt cttcccttcc tttctcgcca cgttcgccgg ctttccccgt caagctctaa     960
atcgggggct ccctttaggg ttccgattta gtgctttacg gcacctcgac cccaaaaaac    1020
ttgattaggg tgatggttca cgtagtgggc catcgccctg atagacggtt tttcgccctt    1080
tgacgttgga gtccacgttc tttaatagtg gactcttgtt ccaaactgga acaacactca    1140
accctatctc ggtctattct tttgatttat aagggatttt gccgatttcg gcctattggt    1200
taaaaaatga gctgatttaa caaaaattta acgcgaattt taacaaaata ttaacgctta    1260
caatttcagg tggcactttt cggggaaatg tgcgcggaac ccctatttgt ttattttct     1320
```

```
aaatacattc aaatatgtat ccgctcatga gacaataacc ctgataaatg cttcaataat    1380
attgaaaaag gaagagtatg agtattcaac atttccgtgt cgcccttatt ccctttttg     1440
cggcattttg ccttcctgtt tttgctcacc cagaaacgct ggtgaaagta aaagatgctg    1500
aagatcagtt gggtgcacga gtgggttaca tcgaactgga tctcaacagc ggtaagatcc    1560
ttgagagttt tcgccccgaa gaacgttttc caatgatgag cacttttaaa gttctgctat    1620
gtggcgcggt attatcccgt attgacgccg ggcaagagca actcggtcgc cgcatacact    1680
attctcagaa tgacttggtt gagtactcac cagtcacaga aaagcatctt acggatggca    1740
tgacagtaag agaattatgc agtgctgcca taaccatgag tgataacact gcggccaact    1800
tacttctgac aacgatcgga ggaccgaagg agctaaccgc ttttttgcac aacatggggg    1860
atcatgtaac tcgccttgat cgttgggaac cggagctgaa tgaagccata ccaaacgacg    1920
agcgtgacac cacgatgcct gtagcaatgg caacaacgtt gcgcaaacta ttaactggcg    1980
aactacttac tctagcttcc cggcaacaat tgatagactg gatggaggcg gataaagttg    2040
caggaccact tctgcgctcg gcccttccgg ctggctggtt tattgctgat aaatctggag    2100
ccggtgagcg tggctctcgc ggtatcattg cagcactggg gccagatggt aagccctccc    2160
gtatcgtagt tatctcacacg acggggagtc aggcaactat ggatgaacga atagacaga    2220
tcgctgagat aggtgcctca ctgattaagc attggtagga attaatgatg tctcgtttag    2280
ataaaagtaa agtgattaac agcgcattag agctgcttaa tgaggtcgga atcgaaggtt    2340
taacaacccg taaactcgcc cagaagctag gtgtagagca gcctacattg tattggcatg    2400
taaaaaataa gcgggctttg ctcgacgcct tagccattga gatgttagat aggcaccata    2460
ctcacttttg cccctttagaa ggggaaagct ggcaagattt tttacgtaat aacgctaaaa    2520
gttttagatg tgctttacta agtcatcgcg atggagcaaa agtacattta ggtacacggc    2580
ctacagaaaa acagtatgaa actctcgaaa atcaattagc cttttttatgc caacaaggtt    2640
tttcactaga gaatgcatta tatgcactca gcgcagtggg gcattttact ttaggttgcg    2700
tattggaaga tcaagagcat caagtcgcta agaagaaag ggaaacacct actactgata    2760
gtatgccgcc attattacga caagctatcg aattatttga tcaccaaggt gcagagccag    2820
ccttcttatt cggccttgaa ttgatcatat gcggattaga aaaacaactt aaatgtgaaa    2880
gtgggtctta aaagcagcat aaccttttc cgtgatggta acttcactag tttaaaagga    2940
tctaggtgaa gatcctttt gataatctca tgaccaaaat cccttaacgt gagttttcgt     3000
tccactgagc gtcagacccc gtagaaaaga tcaaaggatc ttcttgagat cctttttttc    3060
tgcgcgtaat ctgctgcttg caaacaaaaa aaccaccgct accagcggtg gtttgtttgc    3120
cggatcaaga gctaccaact ctttttccga aggtaactgg cttcagcaga gcgcagatac    3180
caaatactgt ccttctagtg tagccgtagt taggccacca cttcaagaac tctgtagcac    3240
cgcctacata cctcgctctg ctaatcctgt taccagtggc tgctgccagt ggcgataagt    3300
cgtgtcttac cgggttggac tcaagacgat agttaccgga taaggcgcag cggtcgggct    3360
gaacggggg ttcgtgcaca cagcccagct tggagcgaac gacctacacc gaactgagat    3420
acctacagcg tgagctatga gaaagcgcca cgcttcccga agggagaaag gcggacaggt    3480
atccggtaag cggcagggtc ggaacaggag agcgcacgag ggagcttcca gggggaaacg    3540
cctggtatct ttatagtcct gtcgggtttc gccacctctg acttgagcgt cgatttttgt    3600
gatgctcgtc aggggggcgg agcctatgga aaaacgccag caacgcggcc ttttacggt     3660
tcctggcctt tgctggcct tttgctcaca tgacccgaca                           3700
```

```
<210> SEQ ID NO 2
<211> LENGTH: 154
<212> TYPE: PRT
<213> ORGANISM: Artificial
<220> FEATURE:
<223> OTHER INFORMATION: Mutein S191.4-B24 of human tear lipocalin with
      binding affinity for IL-4R alpha

<400> SEQUENCE: 2
```

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Ser Ser Val
            20                  25                  30

Thr Pro Met Thr Leu Thr Thr Leu Glu Gly Gly Asn Leu Glu Ala Lys
        35                  40                  45

Phe Thr Ala Gln Arg Ser Gly Arg Trp Gln Glu Tyr Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

```
<210> SEQ ID NO 3
<211> LENGTH: 154
<212> TYPE: PRT
<213> ORGANISM: Artificial
<220> FEATURE:
<223> OTHER INFORMATION: Mutein S351.5-M21 of human tear lipocalin with
      binding affinity for IL-4R alpha

<400> SEQUENCE: 3
```

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Glu Ser Val
            20                  25                  30

Thr Pro Met Thr Leu Thr Thr Leu Glu Gly Gly Asn Leu Glu Ala Lys
        35                  40                  45

Leu Thr Leu Gln Arg Lys Gly Arg Trp Gln Glu Met Lys Asp Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

```
Gln Ser Glu Thr Ser Ser Pro Gly Ser Ala
145                 150
```

<210> SEQ ID NO 4
<211> LENGTH: 154
<212> TYPE: PRT
<213> ORGANISM: Artificial
<220> FEATURE:
<223> OTHER INFORMATION: Mutein S276.2-K04 of human tear lipocalin with
      binding affinity for IL-4R alpha

<400> SEQUENCE: 4

```
Ala Ser Asp Glu Glu Ile Gln Asp Val Ser Gly Thr Trp Tyr Leu Lys
1               5                   10                  15

Ala Met Thr Val Asp Pro Arg Cys Pro Arg Ala Tyr Tyr Ser Ser Val
                20                  25                  30

Thr Pro Met Thr Leu Thr Thr Leu Glu Gly Gly Asn Leu Glu Ala Lys
            35                  40                  45

Phe Thr Ala Gln Arg Ser Gly Arg Trp Gln Lys Tyr Lys Leu Val Leu
        50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

<210> SEQ ID NO 5
<211> LENGTH: 154
<212> TYPE: PRT
<213> ORGANISM: Artificial
<220> FEATURE:
<223> OTHER INFORMATION: Mutein S308.5-K12 of human tear lipocalin with
      binding affinity for IL-4R alpha

<400> SEQUENCE: 5

```
Ala Ser Asp Glu Glu Ile Gln Asp Val Ser Gly Thr Trp Tyr Leu Lys
1               5                   10                  15

Ala Met Thr Val Asp Leu Arg Cys Pro Arg Ala Tyr Tyr Trp Ser Val
                20                  25                  30

Thr Pro Met Thr Leu Thr Thr Leu Glu Gly Gly Asn Leu Glu Ala Lys
            35                  40                  45

Phe Thr Ala Leu Arg Ile Gly Arg Trp Gln Ser Tyr Lys Leu Val Leu
        50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly

```
Ala Ala Gly Ala Arg Gly Leu Ser Thr Glu Ser Ile Leu Ile Pro Arg
        130                 135                 140

Gln Ser Glu Thr Ser Ser Pro Gly Ser Ala
145                 150

<210> SEQ ID NO 6
<211> LENGTH: 154
<212> TYPE: PRT
<213> ORGANISM: Artificial
<220> FEATURE:
<223> OTHER INFORMATION: Mutein S308.5-F08 of human tear lipocalin with
      binding affinity for IL-4R alpha

<400> SEQUENCE: 6

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Val Tyr Asn Ser Val
            20                  25                  30

Thr Pro Met Thr Leu Thr Thr Leu Glu Gly Gly Asn Leu Glu Ala Lys
        35                  40                  45

Phe Thr Ala Gln Arg Lys Gly Arg Trp Gln Lys Tyr Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

<210> SEQ ID NO 7
<211> LENGTH: 154
<212> TYPE: PRT
<213> ORGANISM: Artificial
<220> FEATURE:
<223> OTHER INFORMATION: Mutein S308.5-L4 of human tear lipocalin with
      binding affinity for IL-4R alpha

<400> SEQUENCE: 7

Ala Ser Asp Glu Glu Ile Gln Asp Val Ser Gly Thr Trp Tyr Leu Lys
1               5                   10                  15

Ala Met Thr Val Asp Ser Arg Cys Pro Arg Ala Tyr Tyr Val Ser Val
            20                  25                  30

Thr Pro Met Thr Leu Thr Thr Leu Glu Gly Gly Asn Leu Glu Ala Lys
        35                  40                  45

Phe Thr Ala Ala Arg Ile Gly Arg Trp Gln Ser Tyr Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110
```

-continued

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

<210> SEQ ID NO 8
<211> LENGTH: 154
<212> TYPE: PRT
<213> ORGANISM: Artificial
<220> FEATURE:
<223> OTHER INFORMATION: Mutein S308.5-L20 of human tear lipocalin with
      binding affinity for IL-4R alpha

<400> SEQUENCE: 8

Ala Ser Asp Glu Glu Ile Gln Asp Val Ser Gly Thr Trp Tyr Leu Lys
1               5                   10                  15

Ala Met Thr Val Asp Asn Arg Cys Pro Arg Ala Lys Tyr Asp Ser Val
            20                  25                  30

Thr Pro Met Thr Leu Thr Thr Leu Glu Gly Gly Asn Leu Glu Ala Lys
        35                  40                  45

Phe Thr Ala His Arg Arg Gly Arg Trp Gln Gln Tyr Lys Leu Val Leu
50 55 60

Glu Lys Thr Asp Glu Pro Gly Lys Tyr Thr Ala Ser Gly Gly Arg His
65 70 75 80

Val Ala Tyr Ile Ile Arg Ser His Val Lys Asp His Tyr Ile Phe His
85 90 95

Ser Glu Gly Leu Cys Pro Gly Gln Pro Val Pro Gly Val Trp Leu Val
100 105 110

Gly Arg Asp Pro Lys Asn Asn Leu Glu Ala Leu Glu Asp Phe Glu Lys
115 120 125

Ala Ala Gly Ala Arg Gly Leu Ser Thr Glu Ser Ile Leu Ile Pro Arg
130 135 140

Gln Ser Glu Thr Ser Ser Pro Gly Ser Ala
145 150

<210> SEQ ID NO 9
<211> LENGTH: 154
<212> TYPE: PRT
<213> ORGANISM: Artificial
<220> FEATURE:
<223> OTHER INFORMATION: Mutein S308.5-N1 of human tear lipocalin with binding affinity for IL-4R alpha

<400> SEQUENCE: 9

Ala Ser Asp Glu Glu Ile Gln Asp Val Ser Gly Thr Trp Tyr Leu Lys
1 5 10 15

Ala Met Thr Val Asp Tyr Arg Cys Pro Arg Ala Tyr Tyr His Ser Val
20 25 30

Thr Pro Met Thr Leu Thr Thr Leu Glu Gly Gly Asn Leu Glu Ala Lys
35 40 45

Phe Thr Ala His Arg Ala Gly Arg Trp Gln Lys Tyr Lys Leu Val Leu
50 55 60

Glu Lys Thr Asp Glu Pro Gly Lys Tyr Thr Ala Ser Gly Gly Arg His
65 70 75 80

Val Ala Tyr Ile Ile Arg Ser His Val Lys Asp His Tyr Ile Phe His
85 90 95

-continued

```
Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

<210> SEQ ID NO 10
<211> LENGTH: 154
<212> TYPE: PRT
<213> ORGANISM: Artificial
<220> FEATURE:
<223> OTHER INFORMATION: Mutein S308.3-O10 of human tear lipocalin with binding affinity for IL-4R alpha

<400> SEQUENCE: 10

```
Ala Ser Asp Glu Glu Ile Gln Asp Val Ser Gly Thr Trp Tyr Leu Lys
1               5                   10                  15

Ala Met Thr Val Asp Lys Arg Cys Pro Arg Ala Tyr Tyr Arg Ser Val
            20                  25                  30

Thr Pro Met Thr Leu Thr Thr Leu Glu Gly Gly Asn Leu Glu Ala Lys
        35                  40                  45

Phe Thr Ala Lys Arg Asn Gly Arg Trp Gln Pro Tyr Lys Leu Val Leu
    50                  55                  60

Glu Lys Thr Asp Glu Pro Gly Lys Tyr Thr Ala Ser Gly Gly Arg His
65                  70                  75                  80

Val Ala Tyr Ile Ile Arg Ser His Val Lys Asp His Tyr Ile Phe His
                85                  90                  95

Ser Glu Gly Leu Cys Pro Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150
```

<210> SEQ ID NO 11
<211> LENGTH: 154
<212> TYPE: PRT
<213> ORGANISM: Artificial
<220> FEATURE:
<223> OTHER INFORMATION: Mutein S308.5-N20 of human tear lipocalin with binding affinity for IL-4R alpha

<400> SEQUENCE: 11

```
Ala Ser Asp Glu Glu Ile Gln Asp Val Ser Gly Thr Trp Tyr Leu Lys
1               5                   10                  15

Ala Met Thr Val

Val Ala Tyr Ile Ile Arg Ser His Val Lys Asp His Tyr Ile Phe His
            85                  90                  95

Ser Glu Gly Leu Cys Pro Gly Gln Pro Val Pro Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Ser Ala
145                 150

```
<210> SEQ ID NO 12
<211> LENGTH: 456
<212> TYPE: DNA
<213> ORGANISM: Artificial
<220> FEATURE:
<223> OTHER INFORMATION: Nucleotide sequence of Mutein S276.2-K04 of
      human tear lipocalin with binding affinity for IL-4R alpha

<400> SEQUENCE: 12
gcctcagacg aggagattca ggatgtgtca gggacgtggt atctgaaggc catgacggtg      60 gaccccgct gcccgcgggc gtactacagc tcggtgacac ccatgaccct cacgaccctg     120 gaaggggca acctggaagc caagttcacc gcgcagcggt cgggccggtg cagaagtac      180 aagttggtcc tggagaaaac tgatgagccg gaaaatata ctgcctccgg ggcaggcac      240 gtggcataca tcatcaggtc gcacgtgaag gaccactaca tctttcactc tgagggcctg    300
tgccccgggc agccggtccc aggggtgtgg ctcgtgggca gagacccaa gaacaacctg     360 gaagccttgg aggactttga aaagccgca ggagcccgcg gactcagcac ggagagcatc     420
ctcatcccca ggcagagcga aaccagctct ccaggg                              456

<210> SEQ ID NO 13
<211> LENGTH: 459
<212> TYPE: DNA
<213> ORGANISM: Artificial
<220> FEATURE:
<223> OTHER INFORMATION: Nucleotide sequence of Mutein S308.5-F08 of
      human tear lipocalin with binding affinity for IL-4R alpha

<400> SEQUENCE: 13
gcctcagacg aggagattca ggatgtgtca gggacgtggt atctgaaggc catgacggtg      60
gacagtcgct gcccgcgggc ggtgtacaat tcggtgacac ccatgaccct cacgaccctg    120 gaaggggca acctggaagc caagttcacc gctcagcgga agggccggtg cagaagtac      180 aagttggtcc tggagaaaac tgatgagccg gaaaatata ctgcctccgg ggcaggcac      240 gtggcataca tcatcaggtc gcacgtgaag gaccactaca tctttcactc tgagggcctg    300
tgccccgggc agccggtccc aggggtgtgg ctcgtgggca gagacccaa gaacaacctg     360 gaagccttgg aggactttga aaagccgca ggagcccgcg gactcagcac ggagagcatc     420
ctcatcccca ggcagagcga aaccagctct ccagggagc                           459

<210> SEQ ID NO 14
<211> LENGTH: 456
<212> TYPE: DNA
<213> ORGANISM: Artificial
<220> FEATURE:
<223> OTHER INFORMATION: Nucleotide sequence of Mutein S308.5-L4 of
      human tear lipocalin with binding affinity for IL-4R alpha
```

-continued

<400> SEQUENCE: 14
gcctcagacg aggagattca ggatgtgtca gggacgtggt atctgaaggc catgacggtg 60
gactcgcgct gcccgcgggc gtattacgtg tcggtgacac ccatgaccct cacgaccctg 120
gaagggggca acctggaagc caagttcacc gcggcgcgga ttggccggtg gcagagttac 180
aagttggtcc tggagaaaac tgatgagccg ggaaaataca ctgcctccgg gggcaggcac 240
gtggcataca ttatcaggtc gcacgtgaag gaccactaca tctttcactc tgagggcctg 300
tgccccgggc agccggtccc aggggtgtgg ctcgtgggca gagaccccaa gaacaacctg 360
gaagccttgg aggactttga gaaagccgca ggagcccgcg gactcagcac ggagagcatc 420
ctcatcccca ggcagagcga aaccagctct ccaggg 456

<210> SEQ ID NO 15
<211> LENGTH: 456
<212> TYPE: DNA
<213> ORGANISM: Artificial
<220> FEATURE:
<223> OTHER INFORMATION: Nucleotide sequence of Mutein S308.5-L20 of human tear lipocalin with binding affinity for IL-4R alpha

<400> SEQUENCE: 15
gcctcagacg aggagattca ggatgtgtca gggacgtggt atctgaaggc catgacggtg 60
gacaatcgct gcccgcgggc gaagtacgat tcggtgacac ccatgaccct cacgaccctg 120
gaagggggca acctggaagc caagttcacc gcgcatcggc ggggccggtg gcagcagtac 180
aagttggtcc tggagaaaac tgatgagccg ggaaaataca ctgcctccgg gggcaggcac 240
gtggcataca tcatcaggtc gcacgtgaag gaccactaca tctttcactc tgagggcctg 300
tgccccgggc agccggtccc aggggtgtgg ctcgtgggca gagaccccaa gaacaacctg 360
gaagccttgg aggactttga gaaagccgca ggagcccgcg gactcagcac ggagagcatc 420
ctcatcccca ggcagagcga aaccagctct ccaggg 456

<210> SEQ ID NO 16
<211> LENGTH: 456
<212> TYPE: DNA
<213> ORGANISM: Artificial
<220> FEATURE:
<223> OTHER INFORMATION: Nucleotide sequence of Mutein S308.5-N1 of human tear lipocalin with binding affinity for IL-4R alpha

<400> SEQUENCE: 16
gcctcagacg aggagattca ggatgtgtca gggacgtggt atctgaaggc catgacggtg 60
gactatcgct gcccgcgggc gtattaccat tcggtgacac ccatgaccct cacgaccctg 120
gaagggggca acctggaagc caagttcacc gctcatcggg ctggccggtg gcagaagtac 180
aagttggtcc tggagaaaac tgatgagccg ggaaaataca ctgcctccgg gggcaggcac 240
gtggcataca tcatcaggtc gcacgtgaag gaccactaca tctttcactc tgagggcctg 300
tgccccgggc agccggtccc aggggtgtgg ctcgtgggca gagaccccaa gaacaacctg 360
gaagccttgg aggactttga gaaagccgca ggagcccgcg gactcagcac ggagagcatc 420
ctcatcccca ggcagagcga aaccagctct ccaggg 456

<210> SEQ ID NO 17
<211> LENGTH: 456
<212> TYPE: DNA
<213> ORGANISM: Artificial
<220> FEATURE:
<223> OTHER INFORMATION: Nucleotide sequence of Mutein S308.5-N20 of human tear lipocalin with binding affinity for IL-4R alpha

<400> SEQUENCE: 17

```
gcctcagacg aggagattca ggatgtgtca gggacgtggt atctgaaggc catgacggtg     60
gacgagcgct gcccgcgggc gcattacggg tcggtgacac ccatgaccct cacgaccctg    120
gaagggggca acctggaagc caagttcacc gctatgcggt tgggccggtg gcagaagtac    180
aagttggtcc tggagaaaac tgatgagccg ggaaaataca ctgcctccgg gggcaggcac    240
gtggcataca tcatcaggtc gcacgtgaag gaccactaca tctttcactc tgagggcctg    300
tgccccgggc agccggtccc aggggtgtgg ctcgtgggca gagaccccaa gaacaacctg    360
gaagccttgg aggactttga gaaagccgca ggagcccgcg gactcagcac ggagagcatc    420
ctcatcccca ggcagagcga aaccagctct ccaggg                               456
```

<210> SEQ ID NO 18
<211> LENGTH: 825
<212> TYPE: PRT
<213> ORGANISM: Homo sapiens
<220> FEATURE:
<223> OTHER INFORMATION: Human IL-4 receptor

<400> SEQUENCE: 18

```
Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
```

```
            260                 265                 270
Arg Leu Val Ala Ile Ile Gln Asp Ala Gln Gly Ser Gln Trp Glu
            275                 280                 285
Lys Arg Ser Arg Gly Gln Glu Pro Ala Lys Cys Pro His Trp Lys Asn
290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
                    325                 330                 335
Gly Lys Ser Ala Trp Cys Pro Val Glu Ile Ser Lys Thr Val Leu Trp
                340                 345                 350
Pro Glu Ser Ile Ser Val Val Arg Cys Val Glu Leu Phe Glu Ala Pro
            355                 360                 365
Val Glu Cys Glu Glu Glu Glu Val Glu Glu Lys Gly Ser Phe
            370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
                    405                 410                 415
Glu Glu Asn Gly Gly Phe Cys Gln Gln Asp Met Gly Glu Ser Cys Leu
                420                 425                 430
Leu Pro Pro Ser Gly Ser Thr Ser Ala His Met Pro Trp Asp Glu Phe
            435                 440                 445
Pro Ser Ala Gly Pro Lys Glu Ala Pro Pro Trp Gly Lys Glu Gln Pro
450                 455                 460
Leu His Leu Glu Pro Ser Pro Pro Ala Ser Pro Thr Gln Ser Pro Asp
465                 470                 475                 480
Asn Leu Thr Cys Thr Glu Thr Pro Leu Val Ile Ala Gly Asn Pro Ala
                    485                 490                 495
Tyr Arg Ser Phe Ser Asn Ser Leu Ser Gln Ser Pro Cys Pro Arg Glu
                500                 505                 510
Leu Gly Pro Asp Pro Leu Leu Ala Arg His Leu Glu Glu Val Glu Pro
            515                 520                 525
Glu Met Pro Cys Val Pro Gln Leu Ser Glu Pro Thr Thr Val Pro Gln
530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                    565                 570                 575
Glu Phe Val His Ala Val Glu Gln Gly Gly Thr Gln Ala Ser Ala Val
                580                 585                 590
Val Gly Leu Gly Pro Pro Gly Glu Ala Gly Tyr Lys Ala Phe Ser Ser
            595                 600                 605
Leu Leu Ala Ser Ser Ala Val Ser Pro Glu Lys Cys Gly Phe Gly Ala
            610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
                    645                 650                 655
Leu Asp Arg Glu Pro Pro Arg Ser Pro Gln Ser Ser His Leu Pro Ser
                660                 665                 670
Ser Ser Pro Glu His Leu Gly Leu Glu Pro Gly Glu Lys Val Glu Asp
            675                 680                 685
```

```
Met Pro Lys Pro Pro Leu Pro Gln Glu Gln Ala Thr Asp Pro Leu Val
        690             695                 700

Asp Ser Leu Gly Ser Gly Ile Val Tyr Ser Ala Leu Thr Cys His Leu
705             710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
            740             745                 750

Ser Pro Pro Thr Thr Pro Leu Arg Ala Pro Asp Pro Ser Pro Gly Gly
        755             760                 765

Val Pro Leu Glu Ala Ser Leu Cys Pro Ala Ser Leu Ala Pro Ser Gly
    770             775                 780

Ile Ser Glu Lys Ser Lys Ser Ser Ser Phe His Pro Ala Pro Gly
785             790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 19
<211> LENGTH: 427
<212> TYPE: PRT
<213> ORGANISM: Homo sapiens
<220> FEATURE:
<223> OTHER INFORMATION: human IL-13 receptor alpha 1

<400> SEQUENCE: 19

Met Glu Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
        35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65              70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220
```

```
Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
        290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
                340                 345                 350

Pro Val Ile Val Ala Gly Ala Ile Val Leu Leu Leu Tyr Leu Lys
        355                 360                 365

Arg Leu Lys Ile Ile Ile Phe Pro Pro Ile Pro Asp Pro Gly Lys Ile
370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
                420                 425

<210> SEQ ID NO 20
<211> LENGTH: 176
<212> TYPE: PRT
<213> ORGANISM: Homo sapiens
<220> FEATURE:
<223> OTHER INFORMATION: human tear lipocalin (Tlc)

<400> SEQUENCE: 20

Met Lys Pro Leu Leu Leu Ala Val Ser Leu Gly Leu Ile Ala Ala Leu
1               5                   10                  15

Gln Ala His His Leu Leu Ala Ser Asp Glu Glu Ile Gln Asp Val Ser
                20                  25                  30

Gly Thr Trp Tyr Leu Lys Ala Met Thr Val Asp Arg Glu Phe Pro Glu
            35                  40                  45

Met Asn Leu Glu Ser Val Thr Pro Met Thr Leu Thr Thr Leu Glu Gly
    50                  55                  60

Gly Asn Leu Glu Ala Lys Val Thr Met Leu Ile Ser Gly Arg Cys Gln
65                  70                  75                  80

Glu Val Lys Ala Val Leu Glu Lys Thr Asp Glu Pro Gly Lys Tyr Thr
                85                  90                  95

Ala Asp Gly Gly Lys His Val Ala Tyr Ile Ile Arg Ser His Val Lys
                100                 105                 110

Asp His Tyr Ile Phe Tyr Cys Glu Gly Glu Leu His Gly Lys Pro Val
            115                 120                 125

Arg Gly Val Lys Leu Val Gly Arg Asp Pro Lys Asn Asn Leu Glu Ala
        130                 135                 140

Leu Glu Asp Phe Glu Lys Ala Ala Gly Ala Arg Gly Leu Ser Thr Glu
145                 150                 155                 160
```

```
Ser Ile Leu Ile Pro Arg Gln Ser Glu Thr Cys Ser Pro Gly Ser Asp
            165                 170                 175
```

TEAR LIPOCALIN IN MUTEINS BINDING IL-4 R ALPHA

CROSS-REFERENCE TO RELATED APPLICATIONS

The present application is the U.S. National Stacie of PCT/EP2011/059420, filed Jun. 8, 2011, and published in English as WO 2011/154420 A2 on Dec. 15, 2011, and claims priority to U.S. provisional application No. 61/352,461 filed with the USPTO on Jun. 8, 2010, the entire contents of which is incorporated herein by reference in its entirety.

FIELD OF THE INVENTION

The present invention relates to muteins of human tear lipocalin that bind to IL-4 receptor alpha. The invention also relates to corresponding nucleic acid molecules encoding such a mutein and to a method for their generation. The invention further relates a method for producing such a mutein. Finally, the invention is directed to a pharmaceutical composition that includes such a lipocalin mutein as well as to various uses of the mutein.

BACKGROUND

Proteins that selectively bind to selected targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used. The application of other proteins with defined ligand-binding characteristics, for example the lectins, has remained restricted to special cases.

Additional proteinaceous binding molecules that have antibody-like functions are the members of the lipocalin family, which have naturally evolved to bind ligands. Lipocalins occur in many organisms, including vertebrates, insects, plants and bacteria. The members of the lipocalin protein family (Pervaiz, S., & Brew, K. (1987) *FASEB J.* 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

International patent application WO 99/16873 discloses polypeptides of the lipocalin family with mutated amino acid positions in the region of the four peptide loops, which are arranged at the end of the cylindrical β-barrel structure encompassing the binding pocket, and which correspond to those segments in the linear polypeptide sequence that includes the amino acid positions 28 to 45, 58 to 69, 86 to 99, and 114 to 129 of the bilin-binding protein of *Pieris brassicae*. Members of the lipocalin familiy have been reported to be post-translationally modified, e.g. phosphorylation and glycosylation of tear lipocalin (e.g. You, J., et al. (2010) *Electrophoresis* 31, 1853-1861). Nevertheless no post-translational modification is required for their molecular recognition properties.

International patent application WO 00/75308 discloses muteins of the bilin-binding protein, which specifically bind digoxigenin, whereas the international patent applications WO 03/029463 and WO 03/029471 relate to muteins of the human neutrophil gelatinase-associated lipocalin (hNGAL) and apolipoprotein D, respectively. In order to further improve and fine tune ligand affinity, specificity as well as folding stability of a lipocalin variant various approaches using different members of the lipocalin family have been proposed (Skerra, A. (2001) *Rev. Mol. Biotechnol.* 74, 257-275; Schlehuber, S., and Skerra, A. (2002) *Biophys. Chem.* 96, 213-228), such as the replacement of additional amino acid residues. The PCT publication WO 2006/56464 discloses muteins of human neutrophile gelatinase-associated lipocalin with binding affinity for CTLA-4 in the low nanomolar range.

International patent application WO 2005/19256 discloses muteins of tear lipocalin with at least one binding site for different or the same target ligand and provides a method for the generation of such muteins of human tear lipocalin. According to this PCT application, certain amino acid stretches within the primary sequence of tear lipocalin, in particular the loop regions that include amino acids 7-14, 24-36, 41-49, 53-66, 69-77, 79-84, 87-98, and 103-110 of mature human tear lipocalin, are subjected to mutagenesis in order to generate muteins with binding affinities. The resulting muteins have binding affinities for the selected ligand ($K_D$) in the nanomolar range, in most cases >100 nM. International patent application WO 2008/015239 discloses muteins of tear lipocalin binding a given non-natural ligand, including the IL-4 receptor alpha. Binding affinities are in the nanomolar range, reaching as low as almost $1 \times 10^{-10}$ M in surface plamon resonance experiments.

Human tear lipocalin (TLPC or Tlc), also termed lipocalin-1, tear pre-albumin or von Ebner gland protein, was originally described as a major protein of human tear fluid (approximately one third of the total protein content) but has also been identified in several other secretory tissues including prostate, adrenal gland, thymus, mammary gland, testis, nasal mucosa and tracheal mucosa as well as corticotrophs of the pituitary gland. Homologous proteins have been found in rhesus monkey, chimpanzee, rat, mouse, pig, hamster, cow, dog and horse. Tear lipocalin is an unusual lipocalin member in that it exhibits an unusually broad ligand specificity, when compared to other lipocalins, and in its high promiscuity for relative insoluble lipids (see Redl, B. (2000) *Biochim. Biophys. Acta* 1482, 241-248). This feature of tear lipocalin has been attributed to the protein's function in inhibiting bacterial and fungal growth at the cornea. A remarkable number of lipophilic compounds of different chemical classes such as fatty acids, fatty alcohols, phospholipids, glycolipids and cholesterol are endogenous ligands of this protein. Interestingly, in contrast to other lipocalins the strength of ligand (target) binding correlates with the length of the hydrocarbon tail both for alkyl amides and fatty acids. Thus, tear lipocalin binds most strongly the least soluble lipids (Glasgow, B. J. et al. (1995) *Curr. Eye Res.* 14, 363-372; Gasymov, O. K. et al. (1999) *Biochim. Biophys. Acta* 1433, 307-320). The 1.8-Å crystal structure of tear lipocalin revealed an unusually large cavity inside its β-barrel (Breustedt, D. A. et al. (2005) *J. Biol. Chem.* 280, 1, 484-493).

Despite this progress it would be still desirable to have a human tear lipocalin mutein that has improved binding properties for IL-4 receptor alpha, in particular of higher binding affinity, simply for the reason to further improve the suitability of muteins of human tear lipocalin in diagnostic and therapeutic applications.

SUMMARY OF THE INVENTION

Accordingly, it is an object of the invention to provide a further human tear lipocalin mutein with high binding affinity for IL 4 receptor alpha.

This object is accomplished by a human tear lipocalin mutein with the features set out in the claims, in particular in claim 1.

In a first aspect the present invention provides a mutein of human tear lipocalin. The mutein binds to IL 4 receptor alpha. The mutein includes a mutated amino acid residue at any one or more of the sequence positions 27, 28, 30, 31, 33, 53, 57, 61, 64, 66, 80, 83, 104-106 and 108 of the linear polypeptide sequence of the mature human tear lipocalin. The mutein further includes a mutated amino acid residue at any two or more of the sequence positions 26, 32, 34, 55, 56, 58 and 63 of the linear polypeptide sequence of the mature human tear lipocalin. The amino acid sequence of the mutein of human tear lipocalin includes one of the following sets of amino acid combinations: (1) Ser 26, Glu 34, Leu 55, Lys 58, (2) Ser 26, Asn 34, Ala 55, Lys 58, (3) Ser 26, Val 34, (4) Pro 26, Ser 34 (5) Pro 26, Ala 55, (6) Leu 26, Trp 34, Ala 55, (7) Leu 26, Trp 34, Ile 58, (8) Asn 26, Asp 34, (9) Asn 26, Ala 55, (10) Tyr 26, His 34, Ala 55, (11) Tyr 26, His 34, Ala 58, (12) Lys 26, Arg 34, Ala 55, (13) Lys 26, Arg 34, Asn 58, (14) Glu 26, Gly 34, Ala 55 and (15) Glu 26, Gly 34, Leu 58.

The term "position" when used in accordance with the invention means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the invention which may be substituted may very due to deletion or addition of amino acids elsewhere in a (mutant or wild-type) lipocalin. Similarly, the position of a given nucleotide in accordance with the present invention which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the invention it is preferably to be understood that nucleotides/amino acids may differ in the indicated number but may still have similar neighboring nucleotides/amino acids. Said nucleotides/amino acids which may be exchanged, deleted or added are also comprised by the term "corresponding position".

Specifically, in order to determine whether a nucleotide residue or amino acid residue of the amino acid sequence of a lipocalin different from a Tlc lipocalin mutein of the invention corresponds to a certain position in the nucleotide sequence or the amino acid sequence of a Tlc lipocalin mutein as described, in particular any of SEQ ID NOs: 2-11 or that having one or more amino acid substitutions at position 27, 28, 30, 31, 33, 53, 57, 61, 64, 66, 80, 83, 104-106 and 108 of the linear polypeptide sequence of Tlc (SEQ ID NO: 20), a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a lipocalin mutein of any of SEQ ID Nos: 2-11 or that having one or more amino acid substitutions at position 27, 28, 30, 31, 33, 53, 57, 61, 64, 66, 80, 83, 104-106 and 108 of the linear polypeptide sequence of Tlc (SEQ ID NO: 20) can serve as "subject sequence", while the amino acid sequence of a lipocalin different from Tlc serves as "query sequence".

In a second aspect the present invention provides a method of generating a mutein of human tear lipocalin. The mutein binds to IL-4 receptor alpha. The method includes subjecting a nucleic acid molecule encoding a human tear lipocalin to mutagenesis at any one or more of the amino acid sequence positions 27, 28, 30, 31, 33, 53, 57, 61, 64, 66, 80, 83, 104-106 and 108 of the linear polypeptide sequence of mature human tear lipocalin. Further, the method includes subjecting the nucleic acid molecule encoding a human tear lipocalin to mutagenesis at any two or more of the amino acid sequence positions 26, 32, 34, 55, 56, 58 and 63 of the linear polypeptide sequence of the mature human tear lipocalin. At least one of the two or more of the amino acid sequence positions 26, 32, 34, 55, 56, 58 and 63 of the linear polypeptide sequence of the mature human tear lipocalin. As a result one or more nucleic acids encoding a mutein of human tear lipocalin are obtained. The amino acid sequence of the encoded mutein includes one of the following sets of amino acid combinations: (1) Ser 26, Glu 34, Leu 55, Lys 58, (2) Ser 26, Asn 34, Ala 55, Lys 58, (3) Ser 26, Val 34, (4) Pro 26, Ser 34, (5) Pro 26, Ala 55, (6) Leu 26, Trp 34, Ala 55, (7) Leu 26, Trp 34, Ile 58, (8) Asn 26, Asp 34, (9) Asn 26, Ala 55, (10) Tyr 26, His 34, Ala 55, (11) Tyr 26, His 34, Ala 58, (12) Lys 26, Arg 34, Ala 55, (13) Lys 26, Arg 34, Asn 58, (14) Glu 26, Gly 34, Ala 55, and (15) Glu 26, Gly 34, Leu 58. The method also includes expressing the one or more mutein encoding nucleic acid molecules thus obtained in an expression system. The method thereby includes obtaining one or more muteins. Further the method includes enriching the one or more muteins thus obtained that bind to IL 4 receptor alpha by means of selection and/or isolation.

In a third aspect the present invention provides a nucleic acid molecule. The nucleic acid molecule includes a nucleotide sequence that encodes a mutein according to the first aspect.

In a fourth aspect the present invention provides a host cell. The host cell contains a nucleic acid molecule according to the third aspect.

In a fifth aspect the present invention provides a pharmaceutical composition. The pharmaceutical composition includes a mutein of human tear lipocalin according to the first aspect. The pharmaceutical composition further includes a pharmaceutically acceptable excipient.

The invention will be better understood with reference to the detailed description when considered in conjunction with the non-limiting examples and the accompanying drawings.

DESCRIPTION OF THE FIGURES

FIG. 1 shows the polypeptide sequence of S191.4-B24 (SEQ ID NO:2), a mutein of human tear lipocalin possessing binding affinity for the IL-4 receptor alpha.

FIGS. 2A-2F shows the polypeptide sequences of exemplary muteins with high affinity for IL-4 receptor alpha (SEQ ID NOs: 2-11).

FIG. 4 depicts $IC_{50}$ values of FIG. 3 and data of Biacore® measurements of the binding of a human tear lipocalin muteins of the invention to IL-4 receptor alpha, such as human IL-4 receptor alpha.

DETAILED DESCRIPTION

Figure 3A:
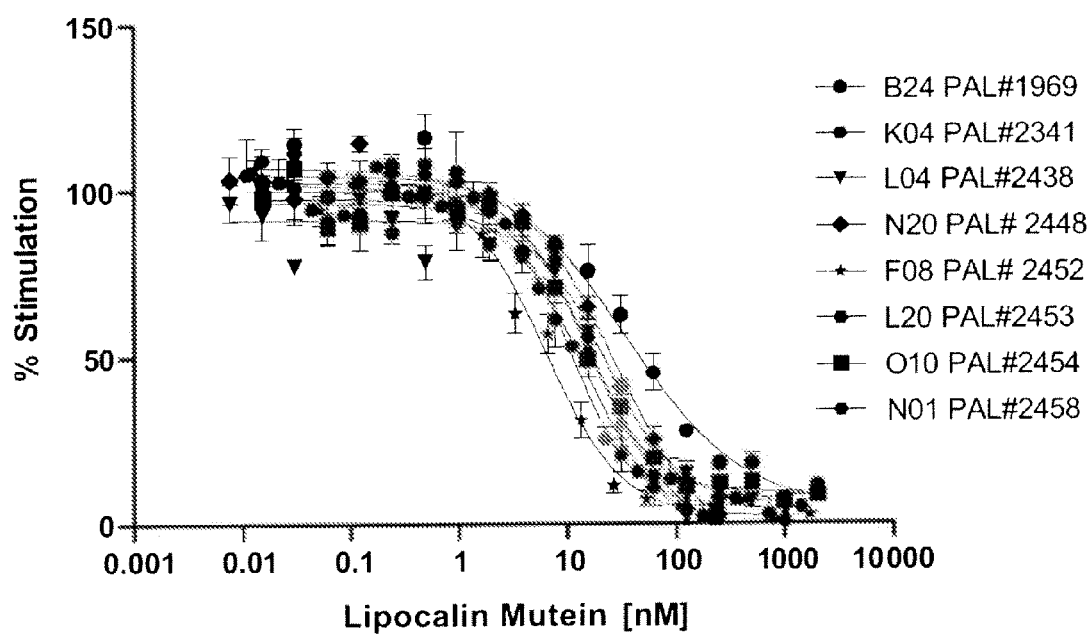
FIGS. 3A-3B show the inhibition of TF-1 cell proliferation by increased amounts of muteins of the invention in the presence of IL-4 (A) and IL-13 (B).

The present invention provides muteins of human tear lipocalin that have a particularly high affinity to IL-4 receptor alpha. IL-4 receptor alpha as a target of a mutein of the present invention is typically a mammalian protein, such as a human protein. In vivo IL-4 receptor alpha can bind interleukin 4 and interleukin 13 to regulate IgE antibody production in B cells.

Binding affinities of muteins according to the invention have been found to be typically of a $K_D$ below 0.1 nM and in some embodiments about 1 picomolar (pM) (cf. FIG. 4). The lipocalin muteins of the invention are accordingly able to bind IL-4 receptor alpha with detectable affinity, i.e. with a dissociation constant of at least 200 nM. In some embodiments a lipocalin mutein of the invention binds IL-4 receptor alpha with a dissociation constant for IL-4 receptor alpha of at least about 10 nM, about 1 nM, about 0.1 nM, about 10 pM or even less. The binding affinity of a mutein to a selected target, in the present case IL-4 receptor alpha, can be measured and thereby $K_D$ values of a mutein-ligand complex be determine by a multitude of methods known to those skilled in the art. Such methods include, but are not limited to, fluorescence titration, competition ELISA, calorimetric methods, such as isothermal titration calorimetry (ITC), and surface plasmon resonance (BIAcore®). Examples for such methods are detailed below (See e.g. Example 2).

Human interleukin-4 receptor alpha chain may have the amino acid sequence of SWISS PROT Data Bank Accession No. P24394 (SEQ ID NO: 18) or of fragments thereof. An illustrative example of a fragment of human interleukin-4 receptor alpha chain includes amino acids 26 to 232 of IL-4 receptor alpha. The amino acid sequence of the human IL-13 receptor alpha 1 is shown in SEQ ID NO: 19.

In general, the term "fragment", as used herein with respect to protein ligands of the tear lipocalin muteins of the invention, relates to N-terminally and/or C-terminally shortened protein or peptide ligands, which retain the capability of the full length ligand to be recognized and/or bound by a mutein according to the invention.

A human tear lipocalin mutein binding IL-4 receptor alpha may act as an IL-4 antagonist and/or IL-13 antagonist or as an inverse IL-4 agonist and/or inverse IL-13 agonist. An inverse agonist binds to the same binding-site as an agonist for a particular receptor and reverses constitutive activity of the respective receptor. So far IL-4 receptors have not been reported to possess intrinsic kinase activity, so that a mutein of the invention may typically act as an IL-4 antagonist and/or IL-13 antagonist. In one embodiment, the human tear lipocalin muteins act as antagonists of human IL-4 and/or human IL-13. In some embodiments the mutein is cross-reactive with the cynomolgus IL-4 IL-4 receptor alpha and as such acts as an antagonist of cynomolgus ligands such as IL-4 and/or IL-13. In some embodiments the mutein is cross-reactive with the marmoset IL-4 IL-4 receptor alpha and as such acts as an antagonist of marmoset ligands such as IL-4 and/or IL-13.

IL-4 receptor alpha can be taken to define a non-natural ligand of human tear lipocalin. The term "non-natural ligand" refers to a compound, which does not bind to native mature human tear lipocalin under physiological conditions. The term "human tear lipocalin" as used herein refers to the mature human tear lipocalin corresponding to the protein of the SWISS-PROT Data Bank Accession Number P31025. Mature human tear lipocalin does not include the N-terminal signal peptide that is included in the sequence of SWISS-PROT Accession Number P31025 (see FIGS. 2A-2F).

The amino acid sequence of a mutein of the invention has a high sequence identity to mature human tear lipocalin when compared to sequence identities with other lipocalins (supra). In this general context the amino acid sequence of a mutein of the invention is at least substantially similar to the amino acid sequence of mature human tear lipocalin. A respective sequence of a mutein of the invention, being substantially similar to the sequences of mature human tear lipocalin, has in some embodiments at least 70%, at least 75%, at least 80%, at least 82%, at least 85%, at least 87%, at least 90% identity, including at least 95% identity to the sequence of mature human tear lipocalin, with the proviso that the altered position or sequence is retained.

By "identity" is meant a property of sequences that measures their similarity or relationship. Identity is measured by dividing the number of identical residues by the total number of residues and multiplying the product by 100. As two illustrative examples, the mutein of the SEQ ID NO: 3 has a sequence identity of 83.3% with the amino acid sequence of mature human tear lipocalin, and the mutein of the SEQ ID NO: 7 has an amino acid sequence identity of 82.0% with mature human tear lipocalin.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "mutated" or "mutant" in reference to a nucleic acid or a polypeptide refers to the exchange, deletion, or insertion of one or more nucleotides or amino acids, respectively, compared to the naturally occurring nucleic acid or polypeptide. A mutein of the present invention includes at least three substitutions in comparison to the corresponding native human tear lipocalin.

In some embodiments a mutein according to the invention includes at least two amino acid substitutions, including 2, 3, 4, 5 or more amino acid substitutions of a native amino acid by an arginine residue. The substituted amino acid may in some embodiments be located at any of positions 27, 30, 57 and 83 with respect to the amino acid sequence of mature human tear lipocalin.

In some embodiments a mutein according to the invention includes an amino acid substitution of a native cysteine residue at positions 61 and/or 153 by a serine residue. In this context it is noted that it has been found that removal of the structural disulfide bond (on the level of a respective naïve nucleic acid library) of wild type tear lipocalin that is formed by the cystein residues 61 and 153 (cf. Breustedt, et al., 2005, supra) provides tear lipocalin muteins that are not only stably folded but in addition are also able to bind a given non-natural ligand with high affinity. Without wishing to be bound by theory, it is also believed that the elimination of the structural disulde bond provides the further advantage of allowing for the (spontaneous) generation or deliberate introduction of non-natural artificial disulfide bonds into muteins of the invention (see Examples), thereby increasing the stability of the muteins, for example. In some embodiments a mutein according to the invention includes an amino acid substitution of a native cysteine residue at position 101 by a serine residue. Further, in some embodiments a mutein according to the invention includes an amino acid substitution of a native arginine residue at positions 111 by a proline residue. In some embodiments a mutein according to the invention includes an amino acid substitution of a native lysine residue at positions 114 by a tryptophan residue.

A mutein of human tear lipocalin according to the invention typically has one of an asparagine, a gutamic acid, a proline, a leucine, a lysine, a serine and a tyrosine at the position that corresponds to amino acid position 26 of mature human tear lipocalin. In some embodiments a mutein of the invention has a sequence in which amino acid position 34 is unchanged relative to mature human tear lipocalin, and where the sequence of the mutein includes the amino acid substitutions Arg 26→Ser, Met 55→Leu, Ser 58→Lys. In some embodiments a mutein of the invention has a sequence that includes the amino acid substitutions Arg 26→Pro and Glu 34→Ser. In some embodiments a mutein of the invention has a sequence that includes the amino acid substitutions Arg 26→Pro and Met 55→Ala. In some embodiments a mutein of the invention has a sequence that includes the amino acid substitutions Arg 26→Ser and Glu 34→Val. In some embodiments a mutein of the invention has a sequence that includes the amino acid substitutions Arg 26→Leu, Glu 34→Trp and Met 55→Ala. In some embodiments a mutein of the invention has a sequence that includes the amino acid substitutions Arg 26→Leu, Glu 34→Trp and Ser 58→Ile. In some embodiments a mutein of the invention has a sequence that includes the amino acid substitutions Arg 26→Ser, Glu 34→Asn, Met 55→Ala, and Ser 58→Lys. In some embodiments a mutein of the invention has a sequence that includes the amino acid substitutions Arg 26→Asn and Glu 34→Asp. In some embodiments a mutein of the invention has a sequence that includes the amino acid substitutions Arg 26→Asn and Met 55→Ala. In some embodiments a mutein of the invention has a sequence that includes the amino acid substitutions Arg 26→Tyr, Glu 34→His and Met 55→Ala. In some embodiments a mutein of the invention has a sequence that includes the amino acid substitutions Arg 26→Tyr, Glu 34→His and Ser 58→Ala. In some embodiments a mutein of the invention has a sequence that includes the amino acid substitutions Arg 26→Lys, Glu 34→Arg and Met 55→Ala. In some embodiments a mutein of the invention has a sequence that includes the amino acid substitutions Arg 26→Lys, Glu 34→Arg and Ser 58→Asn. In some embodiments a mutein of the invention has a sequence that includes the amino acid substitutions Arg 26→Glu, Glu 34→Arg and Met 55→Ala. In some embodiments a mutein of the invention has a sequence that includes the amino acid substitutions Arg 26→Glu, Glu 34→Arg and Ser 58→Leu.

In some embodiments a human tear lipocalin mutein of the invention that binds IL-4 receptor alpha has, when compared to the amino acid sequence of mature human tear lipocalin, a mutated amino acid residue at sequence position 58 or at sequence position 63. In some embodiments the sequence of the mutein of the invention is selected in such a way that, when compared to the amino acid sequence of mature human tear lipocalin, not at both amino acid positions 26 and 34 a serine is present.

The lipocalin mutein may further include with respect to the amino acid sequence of mature human tear lipocalin one or more, including at least two, at least three or at least four amino acid substitutions of native amino acid residues by cysteine residues at any of positions 26-28, 30-34, 53, 55-58, 61, 63, 64, 66, 80, 83, 104-106, and 108 of native mature human tear lipocalin. In some embodiments a mutein according to the invention includes an amino acid substitution of a native amino acid by a cysteine residue at positions 28 or 105 with respect to the amino acid sequence of mature human tear lipocalin. In some embodiments a mutein according to the invention includes an amino acid substitution of a native amino acid by a cysteine residue at positions 28 or 105 with respect to the amino acid sequence of mature human tear lipocalin.

In some embodiments a mutein according to the invention includes a mutated amino acid residue at any three or more, including 3, 4, 5, 6 or 7, of the sequence positions 26, 32, 34, 55, 56, 58 and 63 of the linear polypeptide sequence of the mature human tear lipocalin.

In some embodiments the lipocalin mutein of the invention has a mutated amino acid residue at position 26 that is one of asparagine, glutamine, proline, leucine, lysine, serine and tyrosine. In some embodiments the lipocalin mutein of the invention has a mutated amino acid residue at position 32 that is one of histidine, lysine, tyrosine and valine. In some embodiments the lipocalin mutein of the invention has a mutated amino acid residue at position 34 that is one of arginine, aspartic acid, asparagine, histidine, serine, tryptophan and valine. In some embodiments the lipocalin mutein of the invention has a mutated amino acid residue at position 55 that is one of alanine and leucine. In some embodiments the lipocalin mutein of the invention has a mutated amino acid residue at position 56 that is one of alanine, glutamine, histidine, methionine, leucine and lysine. In some embodiments the lipocalin mutein of the invention has a mutated amino acid residue at position 58 that is one of alanine, arginine, asparagine, histidine, isoleucine and lysine. In some embodiments the lipocalin mutein of the invention has a mutated amino acid residue at position 63 that is one of glutamine, lysine, proline and serine.

In some embodiments a mutein according to the invention includes at least one of the substitutions Met 31→Ala, Leu 33→Tyr, Ser 61→Trp, Asp 80→Ser, Glu 104→Leu, His 106→Pro and Lys 108→Gln. In some embodiments a mutein according to the invention includes two or more, such as 3, 4, 5, 6 or all of the substitutions Met 31→Ala, Leu 33→Tyr, Ser 61→Trp, Asp 80→Ser, Glu 104→Leu, His 106→Pro and Lys 108→Gln. In some embodiments a mutein according to the invention includes a substitution Val 53→Phe or Val 53→Leu. The mutated amino acid residue may also include a substitution Val 64→Tyr or Val 64→Met. It may also include a substitution Ala 66→Leu or Ala 66→Asp.

In some embodiments a mutein of human tear lipocalin according to the invention includes a substituted amino acid of at least one or of both of the cysteine residues occurring at each of the sequences positions 61 and 153 by another amino acid and the mutation of at least three amino acid residue at any one of the sequence positions 26-28, 30-34, 53, 55-58, 63, 64, 66, 80, 83, 104-106, and 108 of the linear polypeptide sequence of mature human tear lipocalin. The positions 26-28 and 30-34 are included in the AB loop, the positions 53 and 55 are located at the very end of a beta-sheet and following positions 56-58 are included in the CD loop. Surprisingly, the positions 63, 64 and 66, are included within a beta-sheet (βD), and the position 80 is located in a α-helical region. Position 83 is a single loop-defining amino acid between this α-helical region and a beta-sheet (βF). The positions 104-106 and 108 are included in the GH loop in the binding site at the open end of the β-barrel structure of tear lipocalin. The definition of these regions is used herein in accordance with Flower (Flower, 1996, supra, Flower, et al., 2000, supra) and Breustedt et al. (2005, supra). Such a mutein may include at least 2, including 3, 4, 5, 6, 8, 10, 12, 14, 15, 16, 17 or 18 mutated amino acid residues at the sequence positions 26-34, 55-58, 63, 64, 80, 83, 104-106, and 108 of the linear polypeptide sequence of mature human tear lipocalin. In some embodiments the mutein includes the amino acid substitutions Cys 61→Ala, Phe, Lys, Arg, Thr, Asn, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds IL-4 receptor alpha and that have the disulphide bridge formed between Cys 61 and Cys 153 are also part of the present invention In some embodiments the mutein includes at least one amino acid substitution, which may be an additional amino acid substitution, selected from Arg 111→Pro and Lys 114→Trp. A mutein of the invention may further include the cysteine at position 101 of the sequence of native mature human tear lipocalin substituted by another amino acid. This substitution may, for example, be the mutation Cys 101→Ser or Cys 101→Thr.

As defined above, a mutein of the invention includes at least one amino acid substitution, which is located at a sequence position of the positions 27, 28, 30, 31, 33, 53, 57, 61, 64, 66, 80, 83, 104-106 and 108 of the linear polypeptide sequence of the mature human tear lipocalin. In some embodiments a mutein of the invention includes two or more, such as 3, 4, 5, 6, 7, 8, 9, 10, 11, 12, 13, 1, 15 or 16 amino acid substitutions of these sequence positions of the mature human tear lipocalin. In one embodiment the mutein has a mutated amino acid residue at each of the sequence positions 27, 28, 30, 31, 33, 53, 57, 61, 64, 66, 80, 83, 104-106 and 108 of the linear polypeptide sequence of the mature human tear lipocalin.

In some embodiments the mutated amino acid residue at any one or more of the sequence positions 27, 28, 30, 31, 33, 53, 57, 61, 64, 66, 80, 83, 104-106 and 108 of the linear polypeptide sequence of the mature human tear lipocalin with respect to the amino acid sequence of mature human tear lipocalin includes one or more of the substitutions Met 31→Ala, Leu 33→Tyr, Ser 61→Trp, Asp 80→Ser, Glu 104→Leu, His 106→Pro and Lys 108→Gln. In some embodiments a mutein of the invention includes two or more, such as 3, 4, 5, 6 or 7 amino acid substitutions of these sequence positions of the mature human tear lipocalin.

In the residual region, i.e. the region differing from sequence positions 26-28, 30-34, 53, 55-58, 63, 64, 66, 80, 83, 104-106, and 108, a lipocalin mutein of the invention may include the wild type (natural) amino acid sequence outside the mutated amino acid sequence positions. In some embodiments a lipocalin mutein according to the invention may also carry one or more amino acid mutations at a sequence position/positions as long as such a mutation does, at least essentially not hamper or not interfere with the binding activity and the folding of the mutein. Such mutations can be accomplished very easily on DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein (see for example, the experimental section in which muteins with truncated N- and C-terminus are generated).

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. Exemplary possibilities of such a mutation to introduce a cysteine residue into the amino acid sequence of a human tear lipocalin mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective tear lipocalin mutein.

The present invention also encompasses muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the sequence of mature human tear lipocalin have been deleted (cf. also the Examples and the attached Sequence Listings). Another possible mutation of the wild type sequence is to change the amino acid sequence at sequence positions 5 to 7 (Ala Ser Asp) to Gly Gly Asp as described in PCT application WO 2005/019256.

In some embodiments a tear lipocalin mutein according to the invention has one or more, including 2, 3, 4, 5, 6, 7, 8, 9, 10, 11 or 12 of the following amino acid substitutions in comparison to mature human tear lipocalin: Glu 27→Arg; Phe 28→Cys; Glu 30→Arg; Met 31→Ala; Leu 33→Tyr; Ile 57→Arg; Ser 61→Trp; Asp 80→Ser; Lys 83→Arg; Glu 104→Leu; Leu 105→Cys; His 106→Pro; Lys 108→Gln. In some embodiments the mutein includes all of these amino acid substitutions. In some embodiments the mutein further includes the set of amino acid substitutions Val 53→Phe, Val 64→Tyr, Ala 66→Leu. In other embodiments the mutein further includes the set of amino acid substitutions Val 53→Leu, Val 64→Met, Ala 66→Asp.

In some embodiments a tear lipocalin mutein according to the invention includes the combination of amino acid substitutions Arg 26→Ser; Asn 32→Tyr; Met 55→Leu; Leu 56→Gln; Ser 58→Lys in comparison to mature human tear lipocalin. In some embodiments a tear lipocalin mutein according to the invention includes the combination of amino acid substitutions Arg 26→Pro; Asn 32→Tyr; Glu 34→Ser; Met 55→Ala; Leu 56→Gln; Glu 63→Lys in comparison to mature human tear lipocalin. In some embodiments a tear lipocalin mutein according to the invention includes the combination of amino acid substitutions Arg 26→Leu; Asn 32→Phe; Glu 34→Trp; Met 55→Ala; Ser 58→Ile; Glu 63→Ser in comparison to mature human tear lipocalin. In some embodiments a tear lipocalin mutein according to the invention includes the combination of amino acid substitutions Arg 26→Ser; Asn 32→Tyr; Glu 34→Val; Met 55→Ala; Leu 56→Ala; Ser 58→Ile; Glu 63→Ser in comparison to mature human tear lipocalin. In some embodiments a tear lipocalin mutein according to the invention includes the combination of amino acid substitutions Arg 26→Ser; Asn 32→Val; Glu 34→Asn; Met 55→Ala; Leu 56→Gln; Ser 58→Lys; Glu 63→Lys in comparison to mature human tear lipocalin. In some embodiments a tear lipocalin mutein according to the invention includes the combination of amino acid substitutions Arg 26→Tyr; Asn 32→Tyr; Glu 34→His; Met 55→Ala; Leu 56→His; Ser 58→Ala; Glu 63→Lys in comparison to mature human tear lipocalin. In some embodiments a tear lipocalin mutein according to the invention includes the combination of amino acid substitutions Arg 26→Lys; Asn 32→Tyr; Glu 34→Arg; Met 55→Ala; Leu 56→Lys; Ser 58→Asn; Glu 63→Pro in comparison to mature human tear lipocalin. In some embodiments a tear lipocalin mutein according to the invention includes the combination of amino acid substitutions Arg 26→Glu; Asn 32→His; Glu 34→Gly; Met 55→Ala; Leu 56→Met; Ser 58→Leu; Glu 63→Lys in comparison to mature human tear lipocalin.

In some embodiments a mutein of the invention includes with respect to the amino acid sequence of mature human tear lipocalin at least 6, 8, 10, 12, 14 or 16 amino acid substitutions selected from the group consisting of Arg 26→Ser, Pro; Glu 27→Arg; Phe 28→Cys; Glu 30→Arg; Met 31→Ala; Asn 32→Tyr, His; Leu 33→Tyr; Glu 34→Gly, Ser, Ala, Asp, Lys, Asn, Thr, Arg; Leu 56→Gln; Ile 57→Arg; Ser 58→Ile, Ala, Arg, Val, Thr, Asn, Lys, Tyr, Leu, Met; Asp 80→Ser; Lys 83→Arg; Glu 104→Leu; Leu 105→Cys; His 106→Pro; and Lys 108→Gln.

Additionally, such a mutein may further include at least one amino acid substitution selected from the group consisting of Met 39→Val; Thr 42→Met, Ala; Thr 43→Ile, Pro, Ala; Glu 45→Lys, Gly; Asn 48→Asp, His, Ser, Thr; Val 53→Leu, Phe, Ile, Ala, Gly, Ser; Thr 54→Ala, Leu; Met 55→Leu, Ala, Ile, Val, Phe, Gly, Thr, Tyr; Glu 63→Lys, Gln, Ala, Gly, Arg; Val 64→Gly, Tyr, Met, Ser, Ala, Lys, Arg, Leu, Asn, His, Thr, Ile; Ala 66→Ile, Leu, Val, Thr, Met; Glu 69→Lys, Gly; Lys 70→Arg, Gln, Glu; Thr 78→Ala; Ile 89→Val; Asp 95→Asn, Ala, Gly; and Tyr 100→His.

In one embodiment the human tear lipocalin mutein binding IL-4 receptor alpha includes the amino acid substitutions: Arg 26→Ser, Glu 27→Arg, Phe 28→Cys, Glu 30→Arg; Met 31→Ala, Leu 33→Tyr, Leu 56→Gln, Ile 57→Arg, Asp 80→Ser, Lys 83→Arg, Glu 104→Leu, Leu 105→Cys, His 106→Pro, and Lys 108→Gln.

In some embodiments the human tear lipocalin mutein binding IL-4 receptor alpha includes one of the following sets of amino acid substitutions:

(1) Arg 26→Ser; Glu 27→Arg; Phe 28→Cys; Glu 30→Arg; Met 31→Ala; Asn 32→Tyr; Leu 33→Tyr; Glu 34→Gly; Leu 56→Gln; Ile 57→Arg; Ser 58→Ile; Asp 80→Ser; Lys 83→Arg; Glu 104→Leu; Leu 105→Cys; His 106→Pro; Lys 108→Gln;

(2) Arg 26→Ser; Glu 27→Arg; Phe 28→Cys; Glu 30→Arg; Met 31→Ala; Asn 32→Tyr; Leu 33→Tyr; Glu 34→Lys; Leu 56→Gln; Ile 57→Arg; Ser 58→Asn; Asp 80→Ser; Lys 83→Arg; Glu 104→Leu; Leu 105→Cys; His 106→Pro; Lys 108→Gln;

(3) Arg 26→Ser; Glu 27→Arg; Phe 28→Cys, Glu 30→Arg; Met 31→Ala; Asn 32→Tyr; Leu 33→Tyr; Leu 56→Gln; Ile 57→Arg; Ser 58→Arg; Asp 80→Ser; Lys 83→Arg; Glu 104→Leu; Leu 105→Cys; His 106→Pro; Lys 108→Gln;

(4) Arg 26→Ser; Glu 27→Arg; Phe 28→Cys; Glu 30→Arg; Met 31→Ala; Asn 32→Tyr; Leu 33→Tyr; Glu 34→Ser; Leu 56→Gln; Ile 57→Arg; Asp 80→Ser; Lys 83→Arg; Glu 104→Leu; Leu 105→Cys; His 106→Pro; Lys 108→Gln;

(5) Arg 26→Ser; Glu 27→Arg; Phe 28→Cys; Glu 30→Arg; Met 31→Ala; Asn 32→His; Leu 33→Tyr; Glu 34→Ser; Leu 56→Gln; Ile 57→Arg; Ser 58→Ala; Asp 80→Ser; Lys 83→Arg; Glu 104→Leu; Leu 105→Cys; His 106→Pro; Lys 108→Gln;

(6) Arg 26→Ser; Glu 27→Arg; Phe 28→Cys; Glu 30→Arg; Met 31→Ala; Asn 32→Tyr; Leu 33→Tyr; Glu 34→Asp; Leu 56→Gln; Ile 57→Arg; Ser 58→Lys; Asp 80→Ser; Lys 83→Arg; Glu 104→Leu; Leu 105→Cys; His 106→Pro; Lys 108→Gln; and (7) Arg 26→Ser; Glu 27→Arg; Phe 28→Cys; Glu 30→Arg; Met 31→Ala; Asn 32→Tyr; Leu 33→Tyr; Glu 34→Gly; Leu 56→Gln; Ile 57→Arg; Asp 80→Ser; Lys 83→Arg; Glu 104→Leu; Leu 105→Cys; His 106→Pro; Lys 108→Gln.

The human tear lipocalin mutein of the invention may include, consist essentially of or consist of any one of the amino acid sequences set forth in SEQ ID NOs: 3-11 or a fragment or variant thereof. The term "fragment" as used herein in connection with the muteins of the invention relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of mature human tear lipocalin and are usually detectable in an immunoassay of mature human tear lipocalin.

The term "variant" as used in the present invention relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

Such a mutein may include with respect to the amino acid sequence of mature human tear lipocalin at least 6, 8, 10, 12, 14 or 16 amino acid substitutions selected from the group consisting of Arg 26→Ser; Glu 27→Ile; Glu 30→Ser; Met 31→Gly; Asn 32→Arg; Leu 33→Ile; Glu 34→Tyr; Leu 56→Lys, Glu, Ala, Met; Ile 57→Phe; Ser 58→Arg; Asp 80→Ser, Pro; Lys 83→Glu, Gly; Glu 104→Leu; Leu 105→Ala; His 106→Val; and Lys 108→Thr and may further include at least one amino acid substitution selected from the group consisting of Leu 41→Phe; Glu 63→Lys; Val 64→Met; Asp 72→Gly; Lys 76→Arg, Glu; Ile 88→Val, Thr; Ile 89→Thr; Arg 90→Lys; Asp 95→Gly; Phe 99→Leu; and Gly 107→Arg, Lys, Glu.

In one specific embodiment, such a mutein includes the amino acid substitutions: Arg 26→Ser, Glu 27→Ile, Glu 30→Ser, Met 31→Gly, Asn 32→Arg, Leu 33→Ile, Glu 34→Tyr, Ile 57→Phe, Ser 58→Arg, Lys 83→Glu, Glu 104→Leu, Leu 105→Ala, His 106→Val, and Lys 108→Thr.

A tear lipocalin mutein of the invention may exist as a monomeric protein. In some embodiments a lipocalin mutein according to the invention may be able to spontaneously dimerise or oligomerise. The use of lipocalin muteins that form stable monomers may be advantageous in some applications, e.g. because of faster diffusion and better tissue penetration. In other embodiments the use of a lipocalin mutein that spontaneously forms stable homodimers or multimers may be advantageous, since such multimers can provide (further) increased affinity and/or avidity to a given target. Furthermore, oligomeric forms of the lipocalin mutein may have slower dissociation rates or prolonged serum half-life. If dimerisation or multimerisation of muteins that form stable monomers is desired, this can for example be achieved by fusing respective oligomerization domains such as jun-fos domains or leucin-zippers to muteins of the invention or by the use of "Duocalins" (see also below).

A lipocalin mutein according to the present invention can be obtained by means of mutagenesis of a naturally occurring form of human tear lipocalin. The term "mutagenesis" as used herein means that the experimental conditions are chosen such that the amino acid naturally occurring at a given sequence position of human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of human tear lipocalin (Redl, B. et al. (1992) *J. Biol. Chem.* 267, 20282-20287) is used as a starting point for the mutagenesis of the peptide segments selected in the present invention. For the mutagenesis of the recited amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-□-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekas B, et al., 1994 *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid that includes the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning. For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a method according to the invention a nucleic acid molecule encoding a human tear lipocalin is firstly subjected to mutagenesis at one or more of the amino acid sequence positions 27, 28, 30, 31, 33, 53, 57, 61, 64, 66, 80, 83, 104-106 and 108 of the linear polypeptide sequence of mature human tear lipocalin. Secondly the nucleic acid molecule encoding a human tear lipocalin is also subjected to mutagenesis at two or more of the amino acid sequence positions 26, 32, 34, 55, 56, 58 and 63 of the linear polypeptide sequence of the mature human tear lipocalin. Of these latter amino acid sequence positions at least one position to be mutated is selected from amino acid sequence position 58 and amino acid sequence position 63.

In one embodiment of the invention, the method for the generation of a mutein of human tear lipocalin includes mutating at least 2, 3, 4, 5, 6, 8, 10, 12, 14, 15, 16, or 17 of the codons of any of the amino acid sequence positions 26-28, 30-34, 53, 55-58, 63, 64, 66, 80, 83, 104-106, and 108 of the linear polypeptide sequence of mature human tear lipocalin. In one embodiment all 22 of the codons of amino acid sequence positions 26, 27, 28, 30, 31, 32, 33, 34, 53, 55, 56, 57, 58, 63, 64, 66, 80, 83, 104, 105, 106, and 108 of the linear polypeptide sequence of mature human tear lipocalin are mutated.

In one embodiment of the afore-mentioned method, additionally at least 2, 3, 4, 5, 6, 8, 10, 12, 14, or 15 of the codons of any of the amino acid sequence positions 26-28, 30-34, 53, 55-58, 63, 64, 66, 80, 83, 104-106, and 108 of the linear polypeptide sequence of mature human tear lipocalin are mutated.

In a further embodiment of the invention, the methods according to the invention include the mutation of both of the codons encoding cysteine at positions 61 and 153 in the linear polypeptide sequence of mature human tear lipocalin. In one embodiment position 61 is mutated to encode an alanine, phenylalanine, lysine, arginine, threonin, asparagine, tyrosine, methionine, serine, proline or a tryptophane residue, to name only a few possibilities. In embodiments where position 153 is mutated, an amino acid such as a serine or alanine can be introduced at position 153.

In another embodiment of the invention as described herein, the codons encoding amino acid sequence positions 111 and/or 114 of the linear polypeptide sequence of mature human tear lipocalin are mutated to encode for example an arginine at position 111 and a tryptophane at position 114.

Another embodiment of the methods of the invention, involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cystein codons at position 61, 101 and 153 are replaced by a codon of another amino acid.

According to the method of the invention a mutein is obtained starting from a nucleic acid encoding human tear lipocalin. Such a nucleic acid is subjected to mutagenesis and introduced into a suitable bacterial or eukaryotic host organism by means of recombinant DNA technology. Obtaining a nucleic acid library of tear lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

The nucleic acid molecule encoding the mutein is expressed using any suitable expression system. The obtained mutein or muteins is/are enriched by means of selection and/or isolation. The selection may for example be carried out under competitive conditions. Competitive conditions as used herein means that selection of muteins encompasses at least one step in which the muteins and the given non-natural ligand of human tear lipocalin, i.e. the IL 4 receptor alpha, are brought in contact in the presence of an additional ligand, which competes with binding of the muteins to IL 4 receptor alpha. This additional ligand may be a physiological ligand of the target, e.g. IL 4, an excess of the target itself or any other non-physiological ligand of the target that binds at least an overlapping epitope to the epitope recognized by the muteins of the invention and thus interferes with target binding of the muteins. Alternatively, the additional ligand competes with binding of the muteins by complexing an epitope distinct from the binding site of the muteins to the target by allosteric effects.

An embodiment of the phage display technique (reviewed in Kay, B. K. et al. (1996), supra; Lowman, H. B. (1997) supra or Rodi, D. J., & Makowski, L. (1999), supra) using temperent M13 phage is given as an example of a selection method that can be employed in the present invention. Another embodiment of the phage display technology that can be used for selection of muteins of the invention is the hyperphage phage technology as described by Broders et al. (Broders et al. (2003) "Hyperphage. Improving antibody presentation in phage display." *Methods Mol. Biol.* 205:295-302). Other temperent phage such as f1 or lytic phage such as T7 may be employed as well. For the exemplary selection method, M13 phagemids are produced which allow the expression of the mutated lipocalin nucleic acid sequence as a fusion protein with a signal sequence at the N-terminus, such as the OmpA-signal sequence, and with the capsid protein pIII of the phage M13 or fragments thereof capable of being incorporated into the phage capsid at the C-terminus. The C-terminal fragment ΔpIII of the phage capsid protein that includes amino acids 217 to 406 of the wild type sequence is may be used to produce the fusion proteins. In one embodiment a C-terminal fragment of pIII is used, in which the cysteine residue at position 201 is missing or is replaced by another amino acid.

Accordingly, a further embodiment of the methods of the invention involves operably fusing a nucleic acid coding for the one or more muteins of human tear lipocalin and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, such as an amber stop codon, is at least partially translated into an amino acid during translation in a suitable suppressor strain.

For example, the phasmid vector pTLPC27, now also called pTlc27 that is described here can be used for the preparation of a phagemid library encoding human tear lipocalin muteins. The inventive nucleic acid molecules coding for the tear lipocalin muteins are inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can for instance be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. One such method is the elution using buffers of pH 2.2, wherein the eluate is subsequently neutralized. Alternatively, a solution of the free target can be added in order to compete with the immobilzed target for binding to the phagemids or target-specific phagemids can be eluted by competition with immunoglobulins or natural liganding proteins which specifically bind to the target of interest.

Afterwards, *E. coli* cells are infected with the eluted phagemids. Alternatively, the nucleic acids can be extracted from the eluted phagemids and used for sequence analysis, amplification or transformation of cells in another manner. Starting from the *E. coli* clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is in some embodiments chosen in such a way that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an *E. coli* strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire tear lipocalin mutein can be subcloned on another expression vector and expressed in a suitable host organism. For example, the vector pTLPC26 now also called pTlc26 can be used for expression in *E. coli* strains such as *E. coli* TG1. A muteins of tear lipocalin thus produced can be purified by various biochemical methods. A tear lipocalin mutein produced, for example with pTlc26, may carry an affinity peptide, a so called affinity tag, for instance at its C-terminus and can therefore be purified by affinity chromatography. Examples of an affinity tag include, but are not limited to biotin, the Strep-tag, Strep-tag II (Schmidt et al., supra), oligohistidine, polyhistidine, an immunoglobulin domain, maltose-binding protein, glutathione-S-transferase (GST) or calmodulin binding peptide (CBP).

Some affinity tags are haptens, for example but not limited to, dinitrophenol and digoxigenin. Some affinity tags are epitope tags, such as the FLAG®-peptide (Asp-Tyr-Lys-Asp-Asp-Asp-Asp-Lys-Gly), the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala, the VSV-G epitope of the Vesicular Stomatitis viral glycoprotein (Cys-Tyr-The-Asp-Ile-Glu-Met-Asn-Arg-Leu-Lys), the E epitope tag of the sequence Gly-Ala-Pro-Val-Pro-Tyr-Pro-Asp-Pro-Leu-Glu-Pro-Arg, the E2 epitope tag of the sequence Gly-Val-Ser-Ser-Thr-Ser-Ser-Asp-Phe-Arg-Asp-Arg, the Tag-100 epitope tag of C-termini of mammalian MAPK/ERK kinases of the sequence Glu-Glu-Thr-Ala-Arg-Phe-Gln-Pro-Gly-Tyr-Arg-Ser, the S-tag of the sequence Lys-Glu-Thr-Ala-Ala-Ala-Lys-Phe-Glu-Arg-Gln-His-Met-Asp-Ser, the "myc" epitope of the transcription factor c-myc of the sequence Glu-Gln-Lys-Leu-Ile-Ser-Glu-Glu-Asp-Leu and the small V5 epitope present on the P and V proteins of the paramyxovirus of Simian Virus 5 (Gly-Lys-Pro-Ile-Pro-Asn-Pro-Leu-Leu-Gly-Leu-Asp-Ser-Thr). In addition, but generally not as a single tag, a solubility-enhancing tag such as NusA, thioredoxin (TRX), small ubiquitin-like modifier (SUMO), and ubiquitin (Ub) may be used. Haptens and epitope tags may be used in combination with a corresponding antibody or an antibody like proteinaceous molecule as binding partner. The S-peptide epitope of the sequence Lys-Glu-Thr-Ala-Ala-Ala-Lys-Phe-Glu-Arg-Gln-His-Met-Asp-Ser may be used as an epitope tag in connection with a respective antibody or in combination with the S-protein as a binding partner (Hackbarth, J S, et al., BioTechniques (2004) 37, 5, 835-839).

The selection can also be carried out by means of other methods. Many corresponding embodiments are known to the person skilled in the art or are described in the literature.

Moreover, a combination of methods can be applied. For example, clones selected or at least enriched by "phage display" can additionally be subjected to "colony screening". This procedure has the advantage that individual clones can directly be isolated with respect to the production of a tear lipocalin mutein with detectable binding affinity for a target.

In addition to the use of *E. coli* as host organism in the "phage display" technique or the "colony screening" method, other bacterial strains, yeast or also insect cells or mammalian cells can be used for this purpose. Further to the selection of a tear lipocalin mutein from a random library as described above, evolutive methods including limited mutagenesis can also be applied in order to optimize a mutein that already possesses some binding activity for the target with respect to affinity or specificity for the target after repeated screening cycles.

It is readily apparent to the skilled person that complex formation is dependent on many factors such as concentration of the binding partners, the presence of competitors, ionic strength of the buffer system etc. Selection and enrichment is generally performed under conditions allowing the isolation of lipocalin muteins having, in complex with the desired target, a dissociation constant of at least 200 nM. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favour fast formation of the complex between the mutein and the target, or in other words a high $k_{on}$ rate. As a further illustrative alternative, the screening can be performed under conditions that select for improved thermostability of the muteins (compared to either wild type tear lipocalin or a mutein that already has affinity towards a pre-selected target).

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis that are suitable for such purposes include random insertion/deletion (RID) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained.

A tear lipocalin mutein of the invention may be used for complex formation with IL 4 receptor alpha. The mutein may also be able to bind an immunogenic fragment of IL 4 receptor alpha. An immunogenic fragment of IL-4 receptor alpha is a fragment that has one or more epitopes, mimotopes or other antigenic determinants, and is thus capable of inducing an immune response or against which an antibody can be raised. The immunogenic fragment may include a single epitope or may have a plurality of epitopes. Since an antigen-presenting system, e.g. a carrier protein, may be used to provide the size required for recognition by an immune system, no particular size limitation applies to the immunogenic fragment. Hence, the immunogenic fragment may also be a "hapten", i.e. a fragment that need not be antigenic per se or may have low immunogenicity, in particular due to its small molecular weight and accordingly size. Typically an immunogenic fragment can, alone or when presented on a carrier, be bound by an immunoglobulin or by a T cell receptor (TCR) if presented by MHC molecules. An immunogenic fragment is typically, alone or when presented in the form of the antigen-presenting system, capable of inducing a humoral immune response and/or cellular immune response leading for instance to the activation of B- and/or T-lymphocytes.

The target of a mutein of the invention is the alpha chain of the interleukin-4 receptor, a transmembrane protein, which contains an extracellular domain of 207 amino acids. A secreted form of the extracellular domain exists, sIL-4R alpha, which is also known as CD124 and capable of blocking IL-4 activities. A mutein of the invention may be able to bind sIL-4 receptor alpha as well as any portion of the extracellular domain of IL 4 receptor alpha.

In this context it is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its ligand) given here may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

Also included in the scope of the present invention are forms of the above muteins, in which the respective mutein has been altered or modified with respect to its potential immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249, 244-250).

Such an approach may also be utilized to identify potential T-cell epitopes in the muteins of the invention and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19, 6, 463-471) and may be adapted to the muteins of the present invention.

The muteins thus obtained may possess a minimized immunogenicity, which is desirable for their use in therapeutic and diagnostic applications, such as those described below.

For some applications, it is also useful to employ the muteins of the invention in a labeled form. Accordingly, the invention is also directed to lipocalin muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to a low molecular weight organic compound. The term "low molecular weight organic compound" as used herein denotes a monomeric carbon-based compound, which may have aliphatic, alicyclic and/or aromatic moieties. In typical embodiments the low molecular weight organic compound is an organic compound that has a main chain of at least two carbon atoms, and in some embodiments not more than 7 or 12 rotatable carbon bonds. Such a compound has a molecular weight in the range from about 100 to about 2000 Dalton, such as from about 100 to about 1000 Dalton. It may optionally include one or two metal atoms.

In general, it is possible to label the lipocalin mutein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the invention may, however, also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al., Diphtheria-toxin receptor-targeted brain drug delivery. *International Congress Series,* 2005 1277, 185-198 or Gaillard P J, et al. Targeted delivery across the blood-brain barrier. *Expert Opin Drug Deliv.* 2005 2, 2, 299-309. Such moieties are for example available under the trade name 2B-Trans™ (to-BBB technologies BV, Leiden, NL).

As indicated above, a mutein of the invention may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partners for extending the half-life of a lipocalin mutein of the invention include albumin (Osborn, B. L. et al., 2002, *J. Pharmacol. Exp. Ther.* 303, 540-548), or an albumin binding protein, for example, a bacterial albumin binding domain, such as the one of streptococcal protein G (Konig, T., & Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself or a biological active fragment of albumin can be used as conjugation partner of a lipocalin mutein of the invention. The term "albumin" includes all mammal albumins such as human serum albumin or bovine serum albumin or rat albumine. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a lipocalin mutein in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of a mutein of the invention is to fuse to the N- or C-terminus of a mutein of the invention long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the invention for the purpose of serum half-life extension.

If one of the above moieties is conjugated to the human tear lipocalin mutein of the invention, conjugation to an amino acid side chain can be advantageous. Suitable amino acid side chains may occur naturally in the amino acid sequence of human tear lipocalin or may be introduced by mutagenesis. In case a suitable binding site is introduced via mutagenesis, one possibility is the replacement of an amino acid at the appropriate position by a cysteine residue. In one embodiment, such mutation includes at least one of Thr 40→Cys, Glu 73→Cys, Arg 90→Cys, Asp 95→Cys or Glu 131→Cys substitution. The newly created cysteine residue at any of these positions can in the following be utilized to conjugate the mutein to moiety prolonging the serum half-life of the mutein, such as PEG or an activated derivative thereof.

In another embodiment, in order to provide suitable amino acid side chains for conjugating one of the above moieties to the muteins of the invention artificial amino acids may be introduced by mutagenesis. Generally, such artificial amino acids are designed to be more reactive and thus to facilitate the conjugation to the desired moiety. One example of such an artifical amino acid that may be introduced via an artificial tRNA is para-acetyl-phenylalanine.

For several applications of the muteins disclosed herein it may be advantageous to use them in the form of fusion proteins. In some embodiments, the inventive human tear lipocalin mutein is fused at its N-terminus or its C-terminus to a protein, a protein domain or a peptide such as a signal sequence and/or an affinity tag.

For pharmaceutical applications a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugates described above, the fusion partner may be an Fc part of an immunoglobulin, a CH3 domain of an immunoglobulin, a CH4 domain of an immunoglubolin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra *J. Pharmacol. Exp. Ther.* 303, 540-548), or an albumin binding protein, for example, a bacterial albumin binding domain, such as the one of streptococcal protein G (König, T., & Skerra, A. (1998) *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" includes all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "Duocalins", cf. Schlehuber, S., and Skerra, A. (2001), Duocalins, engineered ligand-binding proteins with dual specificity derived from the lipocalin fold. *Biol. Chem.* 382, 1335-1342) or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-tag® or Strep-tag® II (Schmidt, T. G. M. et al. (1996) *J. Mol. Biol.* 255, 753-766), the myc-tag, the FLAG®, -tag, the $His_6$-tag® or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP®,) or the yellow fluorescent protein (YFP) are suitable fusion partners for a lipocalin mutein of the invention as well.

The term "fusion protein" as used herein also includes lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. An illustrative signal sequence for secretion a polypeptide into the periplasm of *E. coli* is the OmpA-signal sequence.

The present invention also relates to nucleic acid molecules (DNA and RNA) that include nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but encompasses all nucleic acid molecules that include nucleotide sequences encoding a functional mutein.

Therefore, the present invention also includes a nucleic acid sequence encoding a mutein according to the invention that has a mutation at at least one codon of any of the amino acid sequence positions 26-34, 56-58, 80, 83, 104-106 and 108 of the linear polypeptide sequence of native mature human tear lipocalin, wherein the codons encoding at least one of the cysteine residues at sequence positions 61 and 153 of the linear polypeptide sequence of the mature human tear lipocalin have been mutated to encode any other amino acid residue.

The invention as disclosed herein also includes nucleic acid molecules encoding tear lipocalin muteins, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, such as a promoter sequence.

In some embodiments a nucleic acid molecule of the invention includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques. Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector that includes a nucleic acid molecule encoding a mutein of the invention using established standard methods. The host cell is then cultured under conditions, which allow expression of the heterologous DNA and thus the synthesis of the corresponding polypeptide. Subsequently, the polypeptide is recovered either from the cell or from the cultivation medium.

In some tear lipocalin muteins of the invention, the naturally occurring disulfide bond between Cys 61 and Cys 153 is removed. Accordingly, such muteins (or any other tear lipocalin mutein that does not include an intramolecular disulfide bond) can be produced in a cell compartment having a reducing redox milieu, for example, in the cytoplasma of Gram-negative bacteria. In case a lipocalin mutein of the invention includes intramolecular disulfide bonds, it may be desired to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a mutein of the invention in the cytosol of a host cell, such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, et al. (2002) *J. Mol. Biol.* 315, 1-8).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition, which includes at least one inventive mutein of human tear lipocalin or a fusion protein or conjugate thereof and a pharmaceutically acceptable excipient.

The lipocalin muteins according to the invention can be administered via any parenteral or non-parenteral (enteral) route that is therapeutically effective for proteinaceous drugs. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B (2004) *Am. J. Ther.* 11, 4, 312-316, can also be used for transdermal delivery of the muteins described herein. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the tear lipocalin mutein can be used. However, if wanted, the mutein may also be given in a sustained release formulation, for example liposomal dispersions or hydrogel-based polymer microspheres, like PolyActive™ or OctoDEX™ (Polymers for controlled release, cf. Bos et al., Business Briefing: Pharmatech 2003, 1-6). Other sustained release formulations available are for example PLGA based polymers (PR pharmaceuticals), PLA-PEG based hydrogels (Medincell®) and PEA based polymers (Medivas®).

Accordingly, the muteins of the present invention can be formulated into compositions using pharmaceutically acceptable ingredients as well as established methods of preparation. The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A lipocalin mutein described herein can be administered to an organism, including a human patient per se, or in a pharmaceutical composition where it may include or be mixed with pharmaceutically active ingredients or suitable carriers or excipient(s). Techniques for formulation and administration of a respective lipocalin mutein composition resemble or are identical to those of low molecular weight compounds well established in the art. Exemplary routes include, but are not limited to, oral, transdermal, and parenteral delivery.

A composition that includes a lipocalin mutein of the invention may for instance be applied onto the skin or onto a wound. In some embodiments one may administer a lipocalin mutein or a respective composition in a local rather than systemic manner, for example, via injection.

Pharmaceutical compositions that include a lipocalin mutein of the present invention may be manufactured in a manner that is itself known, e.g., by means of conventional mixing, dissolving, granulating, dragee-making, levigating, emulsifying, encapsulating, entrapping or lyophilizing processes. A pharmaceutical composition for use in accordance with the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the lipocalin mutein or a respective composition may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the lipocalin mutein or a respective composition can be formulated readily by combining them with pharmaceutically acceptable carriers well known in the art. Such carriers enable the lipocalin mutein or a respective composition, as well as a pharmaceutically active compound where present, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration.

The lipocalin mutein may be formulated for parenteral administration by injection, e.g., by intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

The subject in need of such a treatment may be a mammal, such as a human, a dog, a mouse, a rat, a pig, an ape such as cymologous to name only a few illustrative examples. A mutein of the present invention can be use to treat any disease or disorder that involves IL-4 receptor alpha, in the development of such disease or disorder can be displayed to the expression product of a nucleic acid library of the present invention or displayed to otherwise obtained muteins of tear lipocalin.

In this context it is noted that a variety of tumor cells express a greater number of high affinity IL-4 receptors than normal cells. Such cells include solid human tumor such as melanoma, breast cancer, ovarian carcinoma, mesothelioma, glioblastoma, astrocytoma, renal cell carcinoma, head and neck carcinoma, AIDS associated Kaposi's sarcoma=AIDS KS, hormone dependent and independent prostate carcinoma cells, and primary cultures from prostate tumors, for example (cf. Garland, L, et al., (2005) Journal of Immunotherapy 28, 4, 376-381, Rand, R W, et al. Clinical Cancer Research. (2000) 6, 2157-2165; Husain S R, et al. (1999) Nature Medicine 5, 817-822; Puri R K, et al. Cancer Research (1996) 56, 5631-5637; Debinski W, et al, or Husain S R, et al. Cancer Research (1998) 58, 3649-3653, Kawakami K, et al. (2000) Cancer Research, 60, 2981-2987; or Strome S E, et al. Clinical Cancer Research (2002) 8, 281-286, for example. Specific examples of cells with documents overexpression of IL-4 receptors include, but are not limited to, Burkitt lymphoma cell line Jijoye (B-cell lymphom), prostate carcinoma (LN-CaP, DU145), head and neck carcinoma (SCC, KCCT873), Pranceatic cancer (PANC-1 cell line), SCC-25: 13.000 (+/− 500) h head and neck cancer cell line (ATCC). IL4R alpha chain plays a major role in IL4-internalization. Accordingly, when fused or conjugated to a toxin, the tear lipocalin muteins binding to IL-4 Receptor alpha chain can therefore also be used for the treatment of tumors (cancer). Examples of suitable toxins include Pseudomonas exotoxin, pertussis-toxin, diphtheria toxin, ricin, saporin, pseudomonas exotoxin, calicheamicin or a derivative thereof, a taxoid, a maytansinoid, a tubulysin and a dolastatin analogue. Examples of dolastatin analogues include, but are not limited to, auristatin E, monomethylauristatin E, auristatin PYE and auristatin PHE.

For the treatment of cancer, it is also possible to conjugate muteins binding to IL-4 Receptor alpha chain to a cystostatic agent. Examples of such cystostatic agents include Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin.

As is evident from the above disclosure, a mutein of the present invention or a fusion protein or a conjugate thereof can be employed in many applications. In general, such a mutein can be used in all applications antibodies are used, except those with specifically rely on the glycosylation of the Fc part.

Therefore, in another aspect of the invention, the invented muteins of human tear lipocalin are used for the detection of a given non-natural ligand of human tear lipocalin. Such use may include the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins of human tear lipocalin disclosed herein may also be used for the separation of a given non-natural ligand of human tear lipocalin. Such use may include the steps of contacting the mutein with a sample supposed to contain said ligand under suitable conditions, thereby allowing formation of a complex between the mutein and the given ligand, and separating the mutein/ligand complex from the sample.

In both the use of the mutein for the detection of a given non-natural ligand as well as the separation of a given ligand, the mutein and/or the target may be immobilized on a suitable solid phase.

The human tear lipocalin muteins of the invention may also be used to target a compound to a preselected site. For such a purpose the mutein is contacted with the compound of interest in order to allow complex formation. Then the complex that includes the mutein and the compound of interest are delivered to the preselected site. This use is in particular suitable, but not restricted to, for delivering a drug (selectively) to a preselected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the preselected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy. Accordingly, the present invention provides a diagnostic composition comprising an inventive mutein and means for diagnosis such as excipients, buffers, labels (which can be used to label the muteins).

Thus, the present invention also involves the use of the human tear lipocalin muteins of the invention for complex formation with a given non-natural ligand.

Another related use of a mutein described herein is target validation, i.e. the analysis whether a polypeptide assumed to be involved in the development or progress of a disease or disorder is indeed somehow causative of that disease or disorder. This use for validating a protein as a pharmacological drug target takes advantage of the ability of a mutein of the present invention to specifically recognize a surface area of a protein in its native conformation, i.e. to bind to a native epitope. In this respect, it is to be noted that this ability has been reported only for a limited number of recombinant antibodies. However, the use of an inventive mutein for validation of a drug target is not limited to the detection of proteins as targets, but also includes the detection of protein domains, peptides, nucleic acid molecules, organic molecules or metal complexes.

Exemplary Embodiment of the Invention

FIG. 1 shows the primary structure of a previously disclosed human tear lipocalin mutein (S191.4-B24) that exhibits its binding affinity for IL-4 receptor alpha. The first 21 residues (underlined) constitute the signal sequence, which is cleaved upon periplasmic expression. The N-terminal T7-tag (italic) and the C-terminal Streptag-II (bold) are part of the characterized protein. FIG. 1 also shows that 4 N-terminal amino acid residues (His1 His2 Leu3 Ala4) as well as the two last C-terminal amino acid residues (Ser157 and Asp158) of the wild type tear lipocalin are deleted in this mutein.

FIGS. 2A-2F shows the polypeptide sequences of exemplary muteins with high affinity for IL-4 receptor alpha (SEQ ID Nos: 2-11). Numbers indicated by 'SwissProt P31025' show the corresponding amino acid position numbering of the unprocessed precursor sequence of the entry of the SwissProt database. Wt TLc26 essentially corresponds to the sequence of wild type tear lipocalin in the vector pTLc26. However, wt TLc26 does not include a disulfide bond, since the cystein residues at positions 61 and 153 of the mature protein are replaced by serine residues. Likewise, a serine residue at positions 101 of the mature protein is replaced by a serine residue. In addition, at position 111 of the mature protein an arginine residue has been replaced by a proline and at position 114 of the mature protein a lysine residue has been replaced by a tryptophan. Furthermore, the two C-terminal amino acids included in the sequence of SwissProt entry P31025 are not included in the sequence. AB4004 is a randomization library disclosed in international patent application WO 2008/015239, in which the mutated positions are indicated in bold. Randomized sequences are identical to J14 with the exception of position 53 and 55. M3-B24(PSM) indicates hot spots from PSM B24.

Figure 3B:
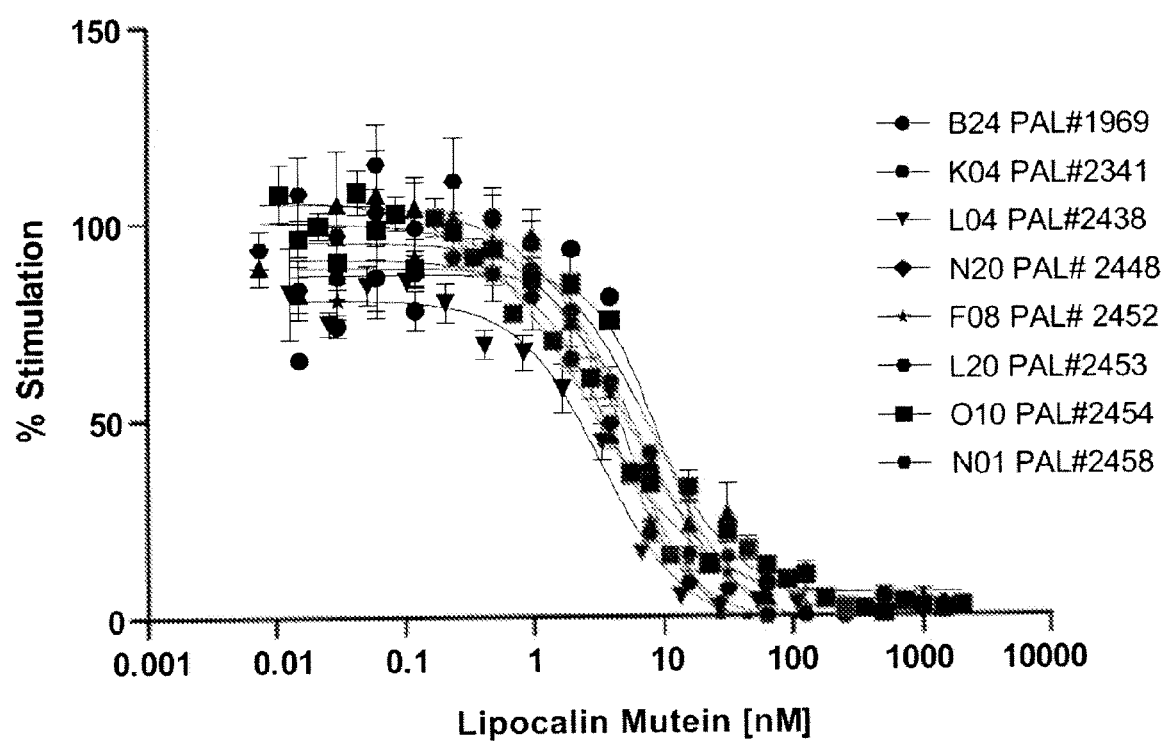

FIGS. 3A-3B show the results of TF-1 cell proliferation assays. TF-1 cells were incubated for 1 hour at 37° C. with the indicated muteins of the invention (S276.2 K04, S308.5 F08, S308.5 N01, S308.5 L20, S308.5 L04, S308.5 N20, S308.3 O10, S191.4 B24 [SEQ ID Nos: 2-11]) in a dilution series before addition of 0.8 ng/ml IL-4 (A) or 12 ng/ml IL-13 (B) for 72 h. Proliferation was measured by $^3$H-thymidine incorporation.

FIG. 4 depicts $IC_{50}$ values from FIG. 3 and results of Biacore® measurements of the muteins of human tear lipocalin with affinity for IL-4 receptor alpha. Approximately 400 RU of IL-4 receptor alpha-Fc was captured on a CM-5 chip, which had previously been coated with an anti human-Fc monoclonal antibody. Subsequently, mutein in a single concentration of 25 nM was passed over the flowcell and changes in resonance units recorded. Reference signals from a flow cell that was equally treated apart from not having any IL-4 receptor alpha-Fc was subtracted and the resulting data fitted to a 1:1 Langmuir model using the BIAevaluation software. Due to the slow dissociation kinetics of the double referencing was used by subtracting the signals from a flow cell that was equally treated apart from not having any IL-4 receptor alpha-Fc and subtracting the signal from an experiment where only sample buffer was injected. The resulting data was fitted to a 1:1 Langmuir model with mass-transport limitation using the BIAevaluation software.

Unless otherwise indicated, established methods in the art of recombinant gene technology were used.

EXAMPLES

Example 1

Affinity Maturation of the Mutein 5191.4-B24 Using a Site-Directed Random Approach A library of variants based on the mutein 5191.4-B24 (SEQ ID NO:2) that is described in PCT application WO 2008/015239 was designed by randomization of the positions 26, 32, 34, 55, 56, 58 and 63 to allow for all 20 amino acids on these positions. The library was constructed essentially as described in Example 1 of WO 2008/015239.

Phagemid selection was carried out as described in Example 2 of WO 2008/015239 using limited target concentration (0.5 nM and 0.1 nM of IL-4 receptor alpha, Peprotech) combined with extended washing times together with a competitive monoclonal antibody against IL-4 receptor alpha (MAB230, R&D Systems; 1 hour washing) or short incubation times (10 minutes), respectively. Three or four rounds of selection were performed.

Preparative production of IL-4 receptor alpha-specific muteins was carried out using *E. coli* K12 strain JM83 harbouring the respective mutein encoded on the expression vector pTLPC10 (SEQ ID No: 1) or, where larger amounts of protein were needed, *E. coil* strain W3110 harbouring the respective expression vector as described in WO 2008/015239.

Example 2

Affinity Measurement Using Biacore®

Affinity measurements were performed essentially as described in Example 9 of WO 2006/56464 with the modifications that approximately 400 RU of IL-4 receptor alpha-Fc (R&D Systems) was immobilized (instead of 2000 RU of human CTLA-4 or murine CTLA-4-Fc used as target in WO 2006/56464) and 100 μl of mutein was injected at a concentration of 25 nM (instead of 40 μl sample purified lipocalin muteins at concentrations of 5-0.3 μM as used in WO 2006/56464).

Example 3

TF-1 Cell Proliferation Assays

IL-4 and IL-13-stimulated TF-1 cell proliferation assays were performed essentially as described in Lefort et al. (Lefort S., et al., (1995) *FEBS Lett.* 366, 2-3, 122-126) and as described in Example 10 of PCT application WO 2008/015239. TF-1 cells were incubated for 1 hour at 37° C. with the indicated muteins of the invention (S276.2 K04, S308.5 F08, S308.5 N01, S308.5 L20, S308.5 L04, S308.5 N20, S308.3 O10, S191.4 B24 [SEQ ID Nos: 3-11]) in a dilution series before addition of 0.8 ng/ml IL-4 (a) or 12 ng/ml IL-13 (b) for 72 h. Proliferation was measured by $^3$H-thymidine incorporation. The results from a TF-1 proliferation assay is depicted in Figure and shows that the high affinity variants S276.2 K04, S308.5 F08, S308.5 N01, S308.5 L20, S308.5 L04, S308.5 N20, and S308.3010 are potent antagonists of IL-4 as well as IL-13 induced signalling and proliferation.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of certain embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A mutein of human tear lipocalin having binding affinity to Interleukin 4 (IL 4) receptor alpha,
wherein with resect to the amino acid sequence of mature human tear lipocalin said mutein comprises a set of amino acid substitutions selected from the group consisting of:
   (1) Arg 26→Ser; Asn 32→Tyr; Met 55→Leu; Leu 56→Gln; and Ser 58→Lys;
   (2) Arg 26→Pro; Asn 32→Tyr; Glu 34→Ser; Met 55→Ala; Leu 56→Gln; and Glu 63→Lys;
   (3) Arg 26→Leu; Asn 32→Phe; Glu 34→Trp; Met 55→Ala; Ser 58→Ile; and Glu 63→Ser;
   (4) Arg 26→Ser; Asn 32→Tyr; Glu 34→Val; Met 55→Ala; Leu 56→Ala; Ser 58→Ile; and Glu 63→Ser;
   (5) Arg 26→Ser; Asn 32→Val; Glu 34→Asn; Met 55→Ala; Leu 56→Gln; Ser 58→Lys; and Glu 63→Lys;
   (6) Arg 26→Asn; Asn 32→Lys; Glu 34→Asp; Met 55→Ala; Leu 56→His; Ser 58→Arg; and Glu 63→Gln;
   (7) Arg 26→Tyr; Asn 32→Tyr; Glu 34→His; Met 55→Ala; Leu 56→His; Ser 58→Ala; and Glu 63→Lys;
   (8) Arg 26→Lys; Asn 32→Tyr; Glu 34→Arg; Met 55→Ala; Leu 56→Lys; Ser 58→Asn; and Glu 63→Pro; and
   (9) Arg 26→Glu; Asn 32→His; Glu 34→Gly; Met 55→Ala; Leu 56→Met; Ser 58→Leu; and Glu 63→Lys.

2. The mutein according to claim 1, wherein the mutein comprises an amino acid substitution of a native amino acid by a cysteine residue at positions 28 or 105 with respect to the amino acid sequence of mature human tear lipocalin.

3. The mutein of claim 1, wherein the mutein comprises a mutated amino acid residue at each of the sequence positions 27, 28, 30, 31, 33, 53, 57, 61, 64, 66, 80, 83, 104-106 and 108 of the linear polypeptide sequence of the mature human tear lipocalin.

4. The mutein of claim 1, wherein the mutated amino acid residue at any one or more of the sequence positions 27, 28, 30, 31, 33, 53, 57, 61, 64, 66, 80, 83, 104-106 and 108 of the linear polypeptide sequence of the mature human tear lipocalin with respect to the amino acid sequence of mature human tear lipocalin comprises at least one of the substitutions Met 31→Ala, Leu 33→Tyr, Ser 61→Trp, Asp 80→Ser, Glu 104→Leu, His 106→Pro and Lys 108→Gln.

5. The mutein of claim 1, wherein the mutated amino acid residue at any one or more of the sequence positions 27, 28, 30, 31, 33, 53, 57, 61, 64, 66, 80, 83, 104-106 and 108 of the linear polypeptide sequence of the mature human tear lipocalin with respect to the amino acid sequence of mature human tear lipocalin comprises a substitution of the group Val 53→Phe, Val 53→Leu, Val 64→Tyr, Val 64→Met, Ala 66→Leu and Ala 66→Asp.

6. The mutein of claim 1, comprising the following amino acid substitutions: Glu 27→Arg; Phe 28→Cys; Glu 30→Arg; Met 31→Ala; Leu 33→Tyr; Ile 57→Arg; Ser 61→Trp; Asp 80→Ser; Lys 83→Arg; Glu 104→Leu; Leu 105→Cys; His 106→Pro; and Lys 108→Gln.

7. The mutein of claim 6, further comprising one of the following sets of amino acid substitutions:
   (1) Val 53→Phe, Val 64→Tyr, Ala 66→Leu; or
   (2) Val 53→Leu, Val 64→Met, Ala 66→Asp.

8. The mutein of claim 1, wherein said mutein comprises the following amino acid substitutions: Arg 26→Pro; Asn 32→Tyr; Glu 34→Ser; Met 55→Ala; Leu 56→Gln; and Glu 63→Lys.

9. The mutein of claim 1, wherein said mutein comprises the following amino acid substitutions: Arg 26→Leu; Asn 32→Phe; Glu 34→Trp; Met 55→Ala; Ser 58→Ile; and Glu 63→Ser.

10. The mutein of claim 1, wherein said mutein comprises the following amino acid substitutions: Arg 26→Ser; Asn 32→Tyr; Glu 34→Val; Met 55→Ala; Leu 56→Ala; Ser 58→Ile; and Glu 63→Ser.

11. The mutein of claim 1, wherein said mutein comprises the following amino acid substitutions; Arg 26→Ser; Asn 32→Val; Glu 34→Asn; Met 55→Ala; Leu 56→Gln; Ser 58→Lys; and Glu 63→Lys.

12. The mutein of claim 1, wherein said mutein comprises the following amino acid substitutions: Arg 26→Asn; Asn 32→Lys; Glu 34→Asp; Met 55→Ala; Leu 56→His; Ser 58→Arg; and Glu 63→Gln.

13. The mutein of claim 1, wherein said mutein comprises the following amino acid substitutions: Arg 26→Tyr; Asn 32→Tyr; Glu 34→His; Met 55→Ala; Leu 56→His; Ser 58→Ala; and Glu 63→Lys.

14. The mutein of claim 1, wherein said mutein comprises the following amino acid substitutions: Arg 26→Lys; Asn 32→Tyr; Glu 34→Arg; Met 55→Ala; Leu 56→Lys; Ser 58→Asn; and Glu 63→Pro.

15. The mutein of claim 1, wherein said mutein comprises the following amino acid substitutions: Arg 26→Glu; Asn 32→His; Glu 34→Gly; Met 55→Ala; Leu 56→Met; Ser 58→Leu; and Glu 63→Lys.

16. The mutein of claim 1, wherein said mutein comprises the amino acid sequence of any one of SEQ ID NOs: 3-11.

17. A method of generating a mutein of human tear lipocalin, wherein the mutein binds to interleukin 4 (IL 4) receptor alpha, comprising:
   (a) subjecting a nucleic acid molecule encoding a human tear lipocalin to mutagenesis at
      (i) any one or more of the amino acid sequence positions 27, 28, 30, 31, 33, 53, 57, 61, 64, 66, 80, 83, 104-106 and 108 of the linear polypeptide sequence of mature human tear lipocalin, and
      (ii) any two or more of the amino acid sequence positions 26, 32, 34, 55, 56, 58 and 63 of the linear polypeptide sequence of the mature human tear lipocalin,
   thereby obtaining one or more nucleic acids encoding a mutein of human tear lipocalin, wherein
      if mutated at position 26, the mutation comprises Ser, Pro, Leu, Asn, Tyr, Lys or Glu;
      if mutated at position 32, the mutation comprises Tyr, Val, Lys or His;
      if mutated at position 34, the mutation comprises Glu, Ser, Trp, Asn, Val, Asp, His, Arg or Gly;
      if mutated at position 55, the mutation comprises Leu or Ala;
      if mutated at position 56, the mutation comprises Gln, Leu, Ala, His, Lys or Met;
      if mutated at position 58, the mutation comprises Lys, Ser, Ile, Arg, Ala, Asn or Leu;

if mutated at position 63, the mutation comprises Glu, Lys, Ser, Gln or Pro (b) expressing the one or more mutein nucleic acid molecule(s) obtained in step (a) in an expression system, thereby obtaining one or more mutein(s); wherein the expression system comprises a bacterial or isolated eukaryotic host cell, or an in vitro translation system and (c) isolating the one or more mutein(s) obtained in step (b) by selecting muteins that bind to IL 4 receptor alpha with a dissociation constant of less than 10 nM.

18. The method according to claim 17, wherein step (c) further comprises:

(ci) providing IL 4 receptor alpha or an immunogenic fragment thereof, and (cii) contacting the one or more muteins with the IL 4 receptor alpha or the immunogenic fragment thereof, thereby allowing the formation of a complex between the IL 4 receptor alpha or the immunogenic fragment thereof and a mutein having binding affinity for the same.

19. The method of claim 17, wherein the selection in step (c) is carried out under competitive conditions.

20. A nucleic acid molecule comprising a nucleotide sequence encoding a mutein of claim 1.

21. An isolated host cell comprising a nucleic acid molecule of claim 20.

* * * * *